(12) United States Patent
Hatchwell et al.

(10) Patent No.: US 8,862,410 B2
(45) Date of Patent: Oct. 14, 2014

(54) COMPOSITIONS AND METHODS FOR DISCOVERY OF CAUSATIVE MUTATIONS IN GENETIC DISORDERS

(75) Inventors: Eli Hatchwell, Winchester (GB); Peggy S. Eis, Fitchburg, WI (US)

(73) Assignee: Population Diagnostics, Inc., Melville, NY (US)

( * ) Notice: Subject to any disclaimer, the term of this patent is extended or adjusted under 35 U.S.C. 154(b) by 0 days.

(21) Appl. No.: 13/196,882

(22) Filed: Aug. 2, 2011

(65) Prior Publication Data

US 2012/0059594 A1   Mar. 8, 2012

Related U.S. Application Data

(60) Provisional application No. 61/370,048, filed on Aug. 2, 2010.

(51) Int. Cl.
| | | |
|---|---|---|
| *G06F 19/00* | (2011.01) | |
| *C12Q 1/68* | (2006.01) | |
| *G06F 19/18* | (2011.01) | |
| *G06F 19/24* | (2011.01) | |

(52) U.S. Cl.
CPC .............. *C12Q 1/6827* (2013.01); *G06F 19/18* (2013.01); *G06F 19/24* (2013.01)
USPC ................... 702/19; 702/20; 703/12; 707/700

(58) Field of Classification Search
CPC ......... G06F 19/18; G06F 19/24; G06F 19/28; G06F 19/22; G06F 19/16; G06F 19/20
See application file for complete search history.

(56) References Cited

U.S. PATENT DOCUMENTS

| | | | |
|---|---|---|---|
| 5,665,549 | A | 9/1997 | Pinkel et al. |
| 5,837,832 | A | 11/1998 | Chee et al. |
| 6,040,138 | A | 3/2000 | Lockhart et al. |
| 6,207,392 | B1 | 3/2001 | Weiss et al. |
| 6,210,878 | B1 | 4/2001 | Pinkel et al. |
| 6,300,063 | B1 | 10/2001 | Lipshutz et al. |
| 6,858,412 | B2 | 2/2005 | Willis et al. |
| 6,916,621 | B2 | 7/2005 | Shah |
| 6,951,761 | B2 | 10/2005 | Star et al. |
| 6,969,589 | B2 | 11/2005 | Patil et al. |
| 6,977,148 | B2 | 12/2005 | Dean et al. |
| 7,011,949 | B2 | 3/2006 | Amorese et al. |
| 7,014,997 | B2 | 3/2006 | Knoll et al. |
| 7,030,231 | B1 | 4/2006 | Craik et al. |
| 7,034,144 | B2 | 4/2006 | Van Dongen et al. |
| 7,424,368 | B2 | 9/2008 | Huang et al. |
| 7,702,468 | B2 | 4/2010 | Chinitz et al. |
| 7,957,913 | B2 | 6/2011 | Chinitz et al. |
| 2002/0012930 | A1 | 1/2002 | Rothberg et al. |
| 2003/0049663 | A1 | 3/2003 | Wigler et al. |
| 2003/0068629 | A1 | 4/2003 | Rothberg et al. |
| 2003/0082606 | A1 | 5/2003 | Lebo et al. |
| 2003/0100102 | A1 | 5/2003 | Rothberg et al. |
| 2003/0148344 | A1 | 8/2003 | Rothberg et al. |
| 2003/0207295 | A1 | 11/2003 | Gunderson et al. |
| 2003/0215821 | A1 | 11/2003 | Gunderson et al. |
| 2004/0018491 | A1 | 1/2004 | Gunderson et al. |
| 2004/0137473 | A1 | 7/2004 | Wigler et al. |
| 2004/0157243 | A1 | 8/2004 | Huang et al. |
| 2004/0197774 | A1 | 10/2004 | Wigler et al. |
| 2004/0248161 | A1 | 12/2004 | Rothberg et al. |
| 2005/0032095 | A1 | 2/2005 | Wigler et al. |
| 2005/0037393 | A1 | 2/2005 | Gunderson et al. |
| 2005/0079510 | A1 | 4/2005 | Berka et al. |
| 2005/0100893 | A1 | 5/2005 | Gunderson et al. |
| 2005/0100932 | A1 | 5/2005 | Lapidus et al. |
| 2005/0112595 | A1 | 5/2005 | Zhao et al. |
| 2005/0124022 | A1 | 6/2005 | Srinivasan et al. |
| 2005/0196799 | A1 | 9/2005 | Wigler et al. |
| 2005/0233339 | A1 | 10/2005 | Barrett et al. |
| 2005/0266444 | A1 | 12/2005 | Wigler et al. |
| 2006/0012784 | A1 | 1/2006 | Ulmer |
| 2006/0012793 | A1 | 1/2006 | Harris |
| 2006/0024678 | A1 | 2/2006 | Buzby |
| 2006/0024711 | A1 | 2/2006 | Lapidus et al. |
| 2006/0063168 | A1 | 3/2006 | Albertson et al. |
| 2006/0078909 | A1 | 4/2006 | Srinivasan et al. |
| 2006/0134674 | A1 | 6/2006 | Huang et al. |
| 2007/0141577 | A1 | 6/2007 | Moore |
| 2007/0207481 | A1 | 9/2007 | Wigler et al. |
| 2007/0259351 | A1 | 11/2007 | Chinitz et al. |
| 2009/0026082 | A1 | 1/2009 | Rothberg et al. |
| 2009/0127589 | A1 | 5/2009 | Rothberg et al. |
| 2009/0304653 | A1 | 12/2009 | Messier |
| 2010/0035252 | A1 | 2/2010 | Rothberg et al. |

(Continued)

FOREIGN PATENT DOCUMENTS

| | | | |
|---|---|---|---|
| WO | WO 2004/044225 A2 | 5/2004 | |
| WO | WO 2005/042763 A2 | 5/2005 | |

(Continued)

OTHER PUBLICATIONS

Berkel, et al. Mutations in the SHANK2 synaptic scaffolding gene in autism spectrum disorder and mental retardation. Nat Genet. Jun. 2010;42(6):489-91. Epub May 16, 2010.

Biomarkers Definitions Working Group. Biomarkers and surrogate endpoints: preferred definitions and conceptual framework. Clin Pharmacol Ther. Mar. 2001;69(3):89-95.

Bochukova, et al. Large, rare chromosomal deletions associated with severe early-onset obesity. Nature. Feb. 4, 2010;463(7281):666-70. Epub Dec. 6, 2009.

Bodmer, et al. Common and rare variants in multifactorial susceptibility to common diseases. Nat Genet. Jun. 2008;40(6):695-701.

(Continued)

*Primary Examiner* — Mary Zeman

(74) *Attorney, Agent, or Firm* — Wilson, Sonsini, Goodrich & Rosati, PC

(57) ABSTRACT

The compositions and methods provided herein allow for identification of causative genetic biomarkers for a disease condition or drug response.

42 Claims, 3 Drawing Sheets

(56) References Cited

U.S. PATENT DOCUMENTS

| | | | |
|---|---|---|---|
| 2010/0137143 | A1 | 6/2010 | Rothberg et al. |
| 2010/0167286 | A1 | 7/2010 | Reijo Pera et al. |
| 2010/0188073 | A1 | 7/2010 | Rothberg et al. |
| 2010/0197507 | A1 | 8/2010 | Rothberg et al. |
| 2010/0227768 | A1 | 9/2010 | Wigler et al. |
| 2010/0248236 | A1 | 9/2010 | Chinitz et al. |
| 2011/0021366 | A1 | 1/2011 | Chinitz et al. |
| 2011/0264376 | A1 | 10/2011 | Chinitz et al. |

FOREIGN PATENT DOCUMENTS

| | | | |
|---|---|---|---|
| WO | WO 2004/044225 | A3 | 4/2006 |
| WO | WO 2007/070640 | A2 | 6/2007 |
| WO | WO 2007/070640 | A3 | 8/2007 |
| WO | WO 2007/129000 | A2 | 11/2007 |
| WO | WO 2007/131135 | A2 | 11/2007 |
| WO | WO 2008/016374 | A2 | 2/2008 |
| WO | WO 2007/129000 | A3 | 3/2008 |
| WO | WO 2007/131135 | A3 | 11/2008 |

OTHER PUBLICATIONS

Conrad, et al. Origins and functional impact of copy number variation in the human genome. Nature. Apr. 1, 2010;464(7289):704-12. Epub Oct. 7, 2009.

Dibbens, et al. Familial and sporadic 15q13.3 microdeletions in idiopathic generalized epilepsy: precedent for disorders with complex inheritance. Hum Mol Genet. Oct. 1, 2009;18(19):3626-31. Epub Jul. 10, 2009.

Estivill, et al. Copy number variants and common disorders: filling the gaps and exploring complexity in genome-wide association studies. PLoS Genet. Oct. 2007;3(10):1787-99.

Freeman, et al. Copy number variation: new insights in genome diversity. Genome Res. Aug. 2006;16(8):949-61. Epub Jun. 29, 2006.

Goldstein. Common genetic variation and human traits. N Engl J Med. Apr. 23, 2009;360(17):1696-8. Epub Apr. 15, 2009.

Helbig, et al. 15q13.3 microdeletions increase risk of idiopathic generalized epilepsy. Nat Genet. Feb. 2009;41(2):160-2. Epub Jan. 11, 2009.

International search report and written opinion dated Apr. 9, 2012 for PCT/US2011/001363.

Itsara, et al. Population analysis of large copy number variants and hotspots of human genetic disease. Am J Hum Genet. Feb. 2009;84(2):148-61. Epub Jan. 22, 2009.

Kallioniemi, et al. Comparative genomic hybridization for molecular cytogenetic analysis of solid tumors. Science. Oct. 30, 1992;258(5083):818-21.

Kimchi-Sarfaty, et al. A "silent" polymorphism in the MDR1 gene changes substrate specificity. Science. Jan. 26, 2007;315(5811):525-8. Epub Dec. 21, 2007.

Kumar, et al. Recurrent 16p11.2 microdeletions in autism. Hum Mol Genet. Feb. 15, 2008;17(4):628-38. Epub Dec. 21, 2007.

Manolio, et al. Finding the missing heritability of complex diseases. Nature. Oct. 8, 2009;461(7265):747-53.

Margulies, et al. Genome sequencing in microfabricated high-density picolitre reactors. Nature. Sep. 15, 2005;437(7057):376-80. Epub Jul. 31, 2005.

Mast, et al. Invader assay for single-nucleotide polymorphism genotyping and gene copy number evaluation. Methods Mol Biol. 2006;335:173-86. Abstract only.

McCarroll, et al. Copy-number variation and association studies of human disease. Nat Genet. Jul. 2007;39(7 Suppl):537-42.

McCarthy, et al. Microduplications of 16p11.2 are associated with schizophrenia. Nat Genet. Nov. 2009;41(11):1223-7. Epub Oct. 25, 2009.

Ozelius, et al. LRRK2 G2019S as a cause of Parkinson's disease in Ashkenazi Jews. N Engl J Med. Jan. 26, 2006;354(4):424-5.

Pang, et al. Towards a comprehensive structural variation map of an individual human genome. Genome Biol. 2010;11(5):R52. Epub May 19, 2010.

Pinkel, et al. High resolution analysis of DNA copy number variation using comparative genomic hybridization to microarrays. Nat Genet. Oct. 1998;20(2):207-11.

Redon, et al. Global variation in copy number in the human genome. Nature. Nov. 23, 2006;444(7118):444-54.

Rodriguez-Revenga, et al. Structural variation in the human genome: the impact of copy number variants on clinical diagnosis. Genet Med. Sep. 2007;9(9):600-6.

Roohi, et al. Disruption of contactin 4 in three subjects with autism spectrum disorder. J Med Genet. Mar. 2009;46(3):176-82. Epub Mar. 18, 2008.

Saha, et al. Technical challenges in using human induced pluripotent stem cells to model disease. Cell Stem Cell. Dec. 4, 2009;5(6):584-95.

Schule, et al. Can cellular models revolutionize drug discovery in Parkinson's disease? Biochim Biophys Acta. Nov. 2009;1792(11):1043-51. Epub Sep. 3, 2009.

Snijders, et al. Assembly of microarrays for genome-wide measurement of DNA copy number. Nature Genet. 2001; 29:263-264.

Soni, et al. Progress toward ultrafast DNA sequencing using solid-state nanopores. Clin Chem. Nov. 2007;53(11):1996-2001. Epub Sep. 21, 2007.

Stefansson, et al. Large recurrent microdeletions associated with schizophrenia. Nature. Sep. 11, 2008;455(7210):232-6.

The International Schizophrenia Consortium. Rare chromosomal deletions and duplications increase risk of schizophrenia. Nature. Sep. 11, 2008;455(7210):237-41. Epub Jul. 30, 2008.

Walsh, et al. Detection of inherited mutations for breast and ovarian cancer using genomic capture and massively parallel sequencing. Proc Natl Acad Sci USA. Jul. 13, 2010;107(28):12629-33. Epub Jun. 28, 2010.

Walsh, et al. Spectrum of mutations in BRCA1, BRCA2, CHEK2, and TP53 in families at high risk of breast cancer. JAMA. Mar. 22, 2006;295(12):1379-88.

Walters, et al. A new highly penetrant form of obesity due to deletions on chromosome 16p11.2. Nature. Feb. 4, 2010;463(7281):671-5.

Weiss, et al. Association between microdeletion and microduplication at 16p11.2 and autism. N Engl J Med. Feb. 14, 2008;358(7):667-75. Epub Jan. 9, 2008.

Zhang, et al. Copy number variation in human health, disease, and evolution. Annu Rev Genomics Hum Genet. 2009;10:451-81.

Bult, et al. The Mouse genome Database (MGD): mouse biology and model systems. Nucleic Acids Research. 2008; 36 Database Issue: D724-D728. doi:10.1093/nar/gkm961.

Office action dated Jul. 17, 2013 for U.S. Appl. No. 12/449,566.

Aitman, et al. Copy number polymorphism in Fcgr3 predisposes to glomerulonephritis in rats and humans. Nature. Feb. 16, 2006;439(7078):851-5.

Bailey, et al. Analysis of Segmental Duplications and Genome Assembly in the Mouse. Genome Res. 2004; 14:789-801.

Bakkaloglu, et al. Molecular cytogenetic analysis and resequencing of contactin associated protein-like 2 in autism spectrum disorders. Am J Hum Genet. Jan. 2008;82(1):165-73.

Cronin, et al. Analysis of genome-wide copy number variation in Irish and Dutch ALS populations. Hum Mol Genet. Nov. 1, 2008;17(21):3392-8. Epub Aug. 7, 2008.

Fernandez, et al. Disruption of contactin 4 (CNTN4) results in developmental delay and other features of 3p deletion syndrome. Addendum. Am J Hum Genet. Jun. 2008;82(6):1385.

Fernandez, et al. Disruption of contactin 4 (CNTN4) results in developmental delay and other features of 3p deletion syndrome. Am J Hum Genet. Jun. 2004;74(6):1286-93.

Gilling, et al. Breakpoint cloning and haplotype analysis indicate a single origin of the common Inv(10)(p11.2q21.2) mutation among northern Europeans. Am. J. Hum. Genet. 2006; 78(5):878-83.

Glessner, et al. Autism genome-wide copy number variation reveals ubiquitin and neuronal genes. Nature. May 28, 2009;459(7246):569-73. Epub Apr. 28, 2009.

Gribble, et al. The complex nature of constitutional de novo apparently balanced translocations in patients presenting with abnormal phenotypes. J. Med. Genet. 2005; 42:8-16.

(56) References Cited

OTHER PUBLICATIONS

Harada, et al. Subtelomere specific microarray based comparative genomic hybridisation: a rapid detection system for cryptic rearrangements in idiopathic mental retardation. J. Med. Genet. 2004; 41:130-136.

Hatchwell, et al. High rate of submicroscopic human genomic polymorphism detected by array CGH. Proceedings of XIX International Genetics Congress. Melbourne, Australia. Abstracts and Posters. 2003; 1.E.0092. pp. 168 and 319.

Hicks et al., "Novel patterns of genome rearrangement and their association with survival in breast cancer," Genome Res 16:1465-1479, 2006.

Huang, et al. Whole genome DNA copy number changes identified by high density oligonucleotide arrays. Hum Genomics. May 2004;1(4):287-99.

Iafrate, et al. Detection of large-scale variation in the human genome. Nature Genet. 2004; 36:949-51.

International Search Report dated Sep. 11, 2008 for PCT Application No. US2007/68183.

Jorde, et al. Population genomics: a bridge from evolutionary history to genetic medicine. Hum. Mol. Genet. 2001; 10(20):2199-2207.

Kumar, et al. A de novo 1p34.2 microdeletion identifies the synaptic vesicle gene RIMS3 as a novel candidate for autism. J Med Genet. Jun. 21, 2009. [Epub ahead of print].

Office action dated Jan. 6, 2011 for U.S. Appl. No. 12/707,561.

Office action dated Sep. 13, 2012 for Chinese Application No. 200780015873.8.

Office action dated Dec. 16, 2008 for U.S. Appl. No. 11/421,348.

Office action dated Jun. 14, 2010 for UK Application No. GB0822081.6.

Office action dated Jun. 2, 2009 for U.S. Appl. No. 11/421,348.

Pinkel, et al. Comparative genomic hybridization. Annu. Rev. Genomics Hum. Genet. 2005; 6:331-54.

Pollack, et al. Microarray analysis reveals a major direct role of DNA copy number alteration in the transcriptional program of human breast tumors. Proc. Natl. Acad. Sci. 2002; 99(20):12963-68.

Sebat, et al. Large-scale copy Number polymorphism in the human genome. Science 2004; 305(5683):525-8.

Sebat, et al. Strong association of de novo copy number mutations with autism. Science. Apr. 20, 2007;316(5823):445-9.

Snijders, et al. Mapping segmental and sequence variations among laboratory mice using BAC array CGH. Genome Res. Feb. 2005;15(2):302-11.

Summary of NRSP-8 Accomplishments: 2003-2008. Available at.http://www.lgu.umd.edu/lgu_v2/pages/attachs/9956_Attach1%20%202003-08%20ACCOMPLISHMENTS.doc. Published on Feb. 9, 2008. (6 pages).

Vissers, et al. Array-based comparative genomic hybridization for the genomewide.detection of submicroscopic chromosomal abnormalities. Am. J. Hum. Genet. 2003;.73:1261-70.

Vissers, et al. Identification of disease genes by whole genome CGH arrays. Hum Mol Genet. Oct. 15, 2005;14 Spec No. 2:R215-223.

Wilson, et al. DNA copy-number analysis in bipolar disorder and schizophrenia reveals aberrations in genes involved in glutamate signaling. Hum Mol Genet. Mar. 1, 2006;15(5):743-9. Epub Jan. 24, 2006.

Office action dated Apr. 3, 2013 for U.S. Appl. No. 13/095,722.

U.S. Appl. No. 14/090,932, filed Nov. 26, 2013, Chinitz et al.

Office action dated May 28, 2014 for U.S. Appl. No. 12/449,566.

Figure 1

New Genome Biology and Disease Theory Concepts

1) Common Disease-Common Variant (CD-CV) vs. Common Disease-Rare Variant (CD-RV) Hypothesis
   OLD – Common variants cause common diseases.
   NEW – Rare variants cause common diseases (Bodmer and Bonilla 2008).
   IMPACT – Genome-wide association studies (GWAS) with SNPs failed to find most causes of disease. New methods are required to find the large number of disease-causing rare variants in a vast background of benign variants.

2) Disease Heterogeneity and Polygenic vs. Complex Multigenic Disease
   OLD – Polygenic theory: a set of common variants of low effect collectively cause a common disease.
   NEW – Complex Multigenic theory: many genes (locus heterogeneity) containing many rare variants (allelic heterogeneity) of high effect independently cause complex diseases. That is, each person has one primary causative mutation (1 variant in 1 gene). Symptoms masquerading as the same disease are often different, unrelated diseases.
   IMPACT – There are no "common" diseases. A complex disease with common symptoms is in actuality a collection of rare diseases. One-size-fits-all medicine is not an option. Multiple causes require multiple therapies.

3) Heterogeneity of Populations
   OLD – Complex diseases have a common cause across multiple ethnicities.
   NEW – Rare variants causative of disease in one ethnic group may be different from those in another.
   IMPACT – Discovery studies in homogeneous populations (e.g., Icelandics, Quebec founders, and Estonians) will not fully solve diseases in other populations because of frequency differences for specific mutations and allelic heterogeneity. Multiethnic studies are required to solve diseases.

4) Human Diversity
   OLD – Any two people are 99.9% the same genetically, or 0.1% different.
   NEW – Any two people are 98.5% the same genetically, or 1.5% different, which is 15X greater than previously known (Pang et al. 2010).
   IMPACT – The spectrum of "normal" variation is much greater than previously known. Finding disease-causing rare variants in the vast background of "normal" variants is enormously challenging even with the latest sequencing technologies.

5) SNPs alone vs. SNVs & SVs (CNVs, InDels...)
   OLD – Single nucleotide polymorphisms (SNPs), present at ≥1% frequency in the population, are the predominant genetic variant contributing to human diversity.
   NEW – Variation is complex, with common and rare variants contributing to diversity. Structural variants (SVs) such as copy number variants (CNVs), insertions/deletions (InDels), and inversions in apparently healthy people and those with disease are a new class of variation. Note, single nucleotide variants (SNVs) are now used as a broader, frequency-independent description of single base changes (i.e., SNPs are a subclass of SNVs).
   IMPACT – CNVs, ranging in size from 1,000 to ~1 million bp, are significant contributors to human diversity and, because of their size, have a greater chance of deleteriously impacting protein structure/expression.

6) **Inherited vs. *De Novo* Variants**
   OLD – Inherited variants are a primary cause of genetic diseases, while *de novo* variants are a minor cause.
   NEW – *De novo* variants frequently cause diseases (i.e., are genetic in origin but classified as sporadic).
   IMPACT – The contribution of *de novo* SVs (e.g., CNVs) to disease is anticipated to be substantial as the currently estimated frequency of *de novo* SVs (Lupski 2007) is 4 orders of magnitude greater than for *de novo* SNVs. Thus, genetic causes of disease (i.e., not just inherited variants, but also including *de novo* variants) may be underestimated.

Figure 3

| | |
|---|---|
| Exon | • Enzyme activity altered or abolished |
| | • Binding site altered or abolished (e.g. neurotransmitter) |
| | • Targeting altered (e.g., membrane protein stays in cytosol) |
| | • Inactive due to protein misfolding (e.g. alternate codon usage) |
| | • Protein Truncated (premature stop codon) |
| Intron | • Alternate exon usage |
| | • Abnormal splice variant |
| | • Protein truncated (premature stop codon) |
| Gene | • Protein truncation or fusion to another protein |
| | • Deletion (1 or no copies) |
| | • Amplification (3 or more copies) |
| Other | • Transcription factor binding altered or abolished |
| | • Chromatin structure altered |
| | • mRNA target expression altered by microRNA (miRNA) (miRNA gene deleted or amplified; miRNA binding site created/abolished) |

COMPOSITIONS AND METHODS FOR DISCOVERY OF CAUSATIVE MUTATIONS IN GENETIC DISORDERS

CROSS REFERENCE

This application claims the benefit of U.S. Patent Provisional Application No. 61/370,048, filed Aug. 2, 2010, which is hereby incorporated by reference it its entirety.

BACKGROUND OF THE INVENTION

Gene expression and function can be modified by variations in copy number. Some variations are found among normal individuals, others occur in the course of normal processes in some species, and still others participate in causing or exacerbating various diseases. For example, many defects in human and non-human animal development are due to gains and losses of chromosomes and chromosomal segments that occur prior to or shortly after fertilization, whereas DNA dosage alterations that occur in somatic cells are often contributors to cancer. Therefore, detection of such aberrations, and interpreting them within the context of broader knowledge, facilitates identification of critical genes and pathways involved in biological processes and diseases, and provides clinically relevant information, such as in identifying efficacious drug regimes.

Copy-number variation presents an opportunity in medical genetics. The importance of normal copy-number variation involving large segments of DNA has been unappreciated until recently. Although methods such as array CGH (array-based comparative genomic hybridization) have established the existence of copy number polymorphisms in human and non-human animal genomes, the picture of this normal variation is incomplete. In results reported to date, measurement noise and resolution have restricted detection to polymorphisms that involve genomic segments of many kilobases or larger, genome coverage has been far from comprehensive, and the population has not been adequately sampled.

A comprehensive understanding of these normal variations is of intrinsic biological interest and is important for the proper interpretation of data and its relation to phenotype. Furthermore, understanding the copy number polymorphisms that are detectable by a particular technique is important so that normal variations are not falsely associated with disease or drug response, and, conversely, to determine if some so-called normal variation can underlie phenotypic characteristics such as disease susceptibility.

As such, the utilization of copy number variants, which can be detected with technologies such as array CGH, genotyping microarrays, and sequencing, is making clear the essential need to understand normal variation throughout human and non-human animal populations. The present invention provides compositions and methods that fill this unmet need for understanding normal variation thus facilitating personalized medicine.

Because of the magnitude of the number of genetic variants that exist and the existence of normal copy number variants and other types of normal genetic variants, sophisticated analysis tools are often used to interpret whether a genetic variant is a causative mutation of a disease or condition. There is thus the need for methods and tools to permit an accurate interpretation or diagnosis of genetic variants of all sizes and types.

SUMMARY OF THE INVENTION

The compositions and methods provided herein allow for identification of causative genetic biomarkers for diseases or conditions, including drug response.

In one aspect the invention discloses a method of determining a causative mutation of a disease or condition in one or more subjects affected by the disease or condition comprising: (a) screening the genome(s) of one or more subjects affected by the disease or condition with an assay to provide information on one or more copy number variants; (b) comparing via a computer, the information on the one or more copy number variants from the genome(s) of the one or more subjects to a compilation of data comprising frequencies of copy number variants in at least 100 subjects unaffected by the disease or condition, wherein said computer comprises computer executable logic that provides instructions for executing said comparison; (c) determining a statistical significance of the one or more copy number variants to a disease or condition associated with a genotype from the comparison of step (b), or determining whether the one or more copy number variants is present in the one or more subjects affected by the disease or condition but not present in the compilation of data from the comparison of step (b); (d) sequencing the one or more copy number variants or genome regions encompassing the one or more copy number variants determined to be statistically significant or present in the genomes of one or more subjects affected by the disease or condition but absent or present at lower frequency in subjects unaffected by the disease or condition according to step (c), in one or more subjects affected by the disease or condition, to identify a first set of one or more genetic variants; (e) sequencing the one or more copy number variants or one or more genome regions encompassing the one or more copy number variants determined to be statistically significant or present in the genomes of one or more subjects affected by the disease or condition but absent or present at lower frequency in subjects unaffected by the disease or condition according to step (c), in at least 100 subjects unaffected by the disease or condition, to identify a second set of one or more genetic variants; (f) determining a statistical significance of the first set of one or more genetic variants by comparing the sequencing information of step (d) to the sequencing information of step (e). In one embodiment the information on the one or more copy number variants is genome-wide. In another embodiment the compilation of data comprising frequencies of copy number variants comprises data from at least 1,000, 3,000, 5,000, or 10,000 subjects unaffected by the disease or condition. In another embodiment screening the first set of one or more genetic variants identified in step (d) is done in at least 100, 200, 500, 1,000, 2,000, 3,000, 4,000, or 5,000 subjects affected by the disease or condition by PCR, junction fragment PCR, multiplex ligation-dependent probe amplification (MLPA), Invader assay, or genotyping microarrays. In another embodiment screening the first set of one or more genetic variants identified in step (d) is done in at least 100, 200, 500, 1,000, 2,000, 3,000, 5,000, 10,000, or 20,000 subjects unaffected by the disease or condition by PCR, junction fragment PCR, multiplex ligation-dependent probe amplification (MLPA), Invader assay, or genotyping microarrays. In another embodiment assessing the functional impact of the one or more copy number variants, the first set of one or more genetic variants, or the second set of one or more genetic variants identified in steps (a), (d), and (e) is done on an RNA or protein product resulting from a gene or functional region of the genome that is near or contains the one or more copy number variants, the first set of one or more genetic variants, or the second set of one or more genetic variants using in silico methods to identify one or more pathogenic variants and benign variants in one or more subjects affected or unaffected by the disease or condition. In another embodiment assessing the functional impact of the one or more copy number variants, the first set of one or more genetic variants, or the second set of one or more genetic variants identified in steps (a), (d), and (e) is done on a gene or functional region of the genome that is near or contains the one or more copy number variants, the first set of one or more genetic variants, or the second set of one or more genetic variants using in vitro methods or assays to identify one or more pathogenic variants and benign variants in one or more subjects affected or unaffected by the disease or condition. In another embodiment assessing the functional impact of the one or more copy number variants, the first set of one or more genetic variants, or the second set of one or more genetic variants identified in steps (a), (d), and (e) is done on a gene or functional region of the genome that is near or contains the one or more copy number variants, the first set of one or more genetic elements, or the second set of one or more genetic elements, using RNAi screening methods or assays to identify one or more pathogenic variants and benign variants in one or more subjects affected or unaffected by the disease or condition. In another embodiment the method further comprises (g) transcriptome sequencing one or more tissues derived from the one or more subjects affected by the disease or condition to provide information on one or more RNA variants resulting from the one or more copy number variants or genome regions encompassing the one or more copy number variants; (h) transcriptome sequencing one or more tissues derived from 20 or more subjects unaffected by the disease or condition to provide information on one or more RNA variants resulting from the one or more copy number variants or genome region(s) encompassing the one or more copy number variant(s); (i) assessing the functional impact of the one or more RNA variants identified in steps (g) and (h) on one or more protein products or regulatory RNA products resulting from the one or more RNA variants using in silico methods to identify one or more pathogenic variants and benign variants in one or more subjects affected or unaffected by the disease or condition. In another embodiment the method further comprises (g) performing epigenetic analysis of one or more tissues derived from the one or more subjects affected by the disease or condition to provide information on the epigenetic state of the region within the one or more copy number variants or genome regions encompassing the one or more copy number variant(s); (h) performing epigenetic analysis of one or more tissues derived from 20 or more subjects unaffected by the disease or condition to provide information on the epigenetic state of the region within the one or more copy number variants or genome regions encompassing the one or more copy number variants; (i) assessing the functional impact of the epigenetic states identified in steps (g) and (h) on one or more RNA or protein products resulting from said epigenetic states contained within or near a gene or functional region of the genome using in silico or in vitro methods to identify one or more pathogenic variants and benign variants in one or more subjects affected or unaffected by the disease or condition. In another embodiment the method further comprises determining a statistical significance of the one or more pathogenic variants. In another embodiment the method further comprises assessing the functional impact of the one or more copy number variants, the first set of one or more genetic variants, or the second set of one or more genetic variants identified in steps (a), (d), and (e) on an RNA or protein product resulting from a gene or functional region of the genome that is near or contains the one or more copy number variants, the first set of one or more genetic variants, or the second set of one or more genetic variants using two or more in silico methods, in vitro methods, RNAi screening methods, transcriptome sequencing, and epigenetic analysis to identify one or more pathogenic variants and benign variants in one or more subjects affected or unaffected by the disease or condition and to determine a statistical significance of the one or more pathogenic variants. In another embodiment the method further comprises assessing the functional impact of the one or more copy number variants, the first set of one or more genetic variants, and the second set of one or more genetic variants identified in steps (a), (d), and (e) on DNA sequence corresponding to a functional region of the genome using in silico methods to identify pathogenic variants and benign variants in one or more subjects affected or unaffected by the disease or condition. In another embodiment the method further comprises the functional impact of the one or more copy number variants, the first set of one or more genetic variants, and the second set of one or more genetic variants identified in steps (a), (d), and (e) on the DNA sequence corresponding to a functional region of the genome using in vitro methods to identify pathogenic variants and benign variants in one or more subjects affected or unaffected by the disease or condition. In another embodiment the method further comprises assessing the functional impact of the one or more copy number variants, the first set of one or more genetic variants, and the second set of one or more genetic variants identified in steps (a), (d), and (e) on the RNA or protein product resulting from a gene or functional region of the genome near or containing the one or more copy number variants, the first set of one or more genetic variants, or the second set of one or more genetic variants using structural biology methods to identify pathogenic variants and benign variants in one or more subjects affected or unaffected by the disease or condition. In another embodiment the method further comprises assessing in silico if an RNA or protein product resulting from a gene near or containing the one or more copy number variants, the first set of one or more genetic variants, or the second set of genetic variants identified in steps (a), (d), and (e) is a known drug target, impacts a known drug target's mechanism of action, is a binding partner of a known drug target, or is linked to a known drug target via pathway analysis. In another embodiment the one or more copy number variants or the first set of one or more genetic variants identified in steps (a) or (d) occur within a gene or impact the expression of a gene wherein said gene is qualified as a drug target via in silico or in vitro methods for potentially treating subjects affected by said disease or condition. In another embodiment the one or more copy number variants or the first set of one or more genetic variants identified in steps (a) or (d) occur within a gene or impact the expression of a gene wherein a binding partner of said gene is qualified as a drug target via in silico or in vitro methods for potentially treating subjects affected by said disease or condition. In another embodiment the one or more copy number variants or the first set of one or more genetic variants identified in steps (a) or (d) occur within a gene or impact the expression of a gene wherein said gene's pathway interaction is identified to another gene that is qualified as a drug target via in silico or in vitro methods for potentially treating subjects affected by said disease or condition. In another embodiment the method further comprises using tissue from the one or more subjects with said disease or condition containing the one or more copy number variants or first set of one or more genetic variants identified in steps (a) or (d) to generate induced pluripotent stems cells for functional validation of the one or more copy number variants or the first set of one or more genetic variants identified in steps (a) or (d) using in vitro methods. In another embodiment the method further comprises (g) transcriptome sequencing one or more tissues derived from the one or more subjects affected by the disease or condition to provide information on one or more RNA variants resulting from the one or more copy number variants or genome regions encompassing the one or more copy number variants; (h) transcriptome sequencing one or more tissues derived from 20 or more subjects unaffected by the disease or condition to provide information on one or more RNA variants resulting from the one or more copy number variants or genome regions encompassing the one or more copy number variants; and (i) assessing the relative expression level or number of RNA variants identified in steps (g) and (h) to identify pathogenic variants and benign variants in one or more subjects affected or unaffected by the disease or condition. In another embodiment the method further comprises (g) performing microarray analysis of one or more tissues derived from the one or more subjects affected by the disease or condition to provide information on one or more RNA variants resulting from the one or more copy number variants or genome regions encompassing the one or more copy number variants; (h) performing microarray analysis of one or more tissues derived from 20 or more subjects unaffected by the disease or condition to provide information on one or more RNA variants resulting from the one or more copy number variants or genome regions encompassing the one or more copy number variants; and (i) assessing the relative expression level or number of RNA variants identified in steps (g) and (h) to identify pathogenic variants and benign variants in one or more subjects affected or unaffected by the disease or condition. In another embodiment the method further comprises (g) performing reverse transcriptase PCR analysis of one or more tissues derived from the one or more subjects affected by the disease or condition to provide information on one or more RNA variants resulting from the one or more copy number variants or genome regions encompassing the one or more copy number variants; (h) performing reverse transcriptase PCR analysis of one or more tissues derived from 20 or more subjects unaffected by the disease or condition to provide information on one or more RNA variants resulting from the one or more copy number variants or genome regions encompassing the one or more copy number variants; and (i) assessing the relative expression level or number of RNA variants identified in steps (g) and (h) to identify pathogenic variants and benign variants in one or more subjects affected or unaffected by the disease or condition. In another embodiment the method further comprises (g) performing Invader assay analysis of one or more tissues derived from one or more subjects affected by the disease or condition to provide information on one or more RNA variants resulting from the one or more copy number variants or genome regions encompassing the one or more copy number variant(s); (h) performing Invader analysis of one or more tissues derived from 20 or more subjects unaffected by the disease or condition to provide information on one or more RNA variants resulting from the one or more copy number variants or genome regions encompassing the one or more copy number variant(s); (i) assessing the relative expression level or number of RNA variants identified in steps (g) and (h) to identify pathogenic variants and benign variants in one or more subjects affected or unaffected by the disease or condition. In another embodiment the information from steps (c) or (f) is used to enroll or exclude a subject with a disease or condition from a therapeutic clinical trial. In another embodiment the information from steps (c) or (f) is used to enroll or exclude a subject with a disease or condition from a diagnostic test clinical trial. In another embodiment the information from steps (a) or (d) is preexisting and stored on a computer comprising computer executable logic that provides instructions for executing said comparisons in steps (c) and (f). In another embodiment the information is stored as part of, or linked to, a subject's electronic medical record or electronic health record. In another embodiment the assay comprises array Comparative Genomic Hybridization, Single Nucleotide Polymorphism genotyping microarray, Single Nucleotide Variant genotyping microarray, sequencing, Fluorescence in Situ Hybridization, PCR, Invader assay, or array-based Invader assay.

In another aspect a method is disclosed for detecting and reporting one or more causative mutations of a disease or condition comprising: (a) screening the genome of a subject with the disease or condition with an assay, (b) determining if the subject has one or more causative mutations, wherein the one or more causative mutations are identified by a method described above; and (c) producing an electronic or hard copy report from indicating whether the one or more causative mutations of said disease or condition is present or absent in the genome of the subject being tested. In one embodiment only a subset of a plurality of causative mutations for a disease or condition is tested for the purpose of diagnosing said disease or condition in a subject, wherein said subset of causative mutations has been previously determined based on: (a) ascertainment of the frequency of occurrence of causative mutations in subjects affected and unaffected with the disease or condition; and/or (b) ascertainment of the pathogenicity of causative mutations in subjects affected with the disease or condition. In another embodiment the genome of the subject is screened only if the subject does not have a subset of causative mutations previously determined based on: (a) ascertainment of the frequency of occurrence of causative mutations in subjects affected and unaffected with the disease or condition; and/or (b) ascertainment of the pathogenicity of causative mutations in subjects affected with the disease or condition. In another embodiment the subject is a newborn. In another embodiment the method further comprises screening small molecule compound libraries to identify one or more compounds that impact the activity or expression of said drug target.

In another aspect a method is disclosed of identifying a pathogenic mutation of a disease or condition in one or more subjects affected by said disease or condition comprising: (a) providing one or more copy number variants associated with said disease or condition in said one or more subjects affected by said disease or condition; and (b) identifying said pathogenic mutation by sequencing said one or more copy number variants and a portion of the genetic material upstream and/or downstream of said copy number variant. In another embodiment the method further comprises screening small molecule compound libraries to identify one or more compounds that impact the activity or expression of said drug target.

In another aspect a computer readable medium is disclosed comprising instructions for determining a causative mutation or a disease or condition in one or more subjects affected by the disease or condition, said instructions comprising the steps of: (a) screening the genome(s) of one or more subjects affected by the disease or condition with an assay to provide information on one or more copy number variants; (b) comparing via a computer, the information on the one or more copy number variants from the genome(s) of the one or more subjects to a compilation of data comprising frequencies of copy number variants in at least 100 subjects unaffected by the disease or condition, wherein said computer comprises computer executable logic that provides instructions for executing said comparison; (c) determining a statistical significance of the one or more copy number variants to a disease or condition associated with a genotype from the comparison of step (b), or determining whether the one or more copy number variants is present in the one or more subjects affected by the disease or condition but not present in the compilation of data from the comparison of step (b); (d) sequencing the one or more copy number variants or genome regions encompassing the one or more copy number variants determined to be statistically significant or present in the genomes of one or more subjects affected by the disease or condition but absent or present at lower frequency in subjects unaffected by the disease or condition according to step (c), in one or more subjects affected by the disease or condition, to identify a first set of one or more genetic variants; (e) sequencing the one or more copy number variants or one or more genome regions encompassing the one or more copy number variants determined to be statistically significant or present in the genomes of one or more subjects affected by the disease or condition but absent or present at lower frequency in subjects unaffected by the disease or condition according to step (c), in at least 100 subjects unaffected by the disease or condition, to identify a second set of one or more genetic variants; (f) determining a statistical significance of the first set of one or more genetic variants by comparing the sequencing information of step (d) to the sequencing information of step (e).

In another aspect a computer system comprising instructions is disclosed for determining a causative mutation or a disease or condition in one or more subjects affected by the disease or condition, said system comprising instructions for executing the steps of: (a) screening the genome(s) of one or more subjects affected by the disease or condition with an assay to provide information on one or more copy number variants; (b) comparing via a computer, the information on the one or more copy number variants from the genome(s) of the one or more subjects to a compilation of data comprising frequencies of copy number variants in at least 100 subjects unaffected by the disease or condition, wherein said computer comprises computer executable logic that provides instructions for executing said comparison; (c) determining a statistical significance of the one or more copy number variants to a disease or condition associated with a genotype from the comparison of step (b), or determining whether the one or more copy number variants is present in the one or more subjects affected by the disease or condition but not present in the compilation of data from the comparison of step (b); (d) sequencing the one or more copy number variants or genome regions encompassing the one or more copy number variants determined to be statistically significant or present in the genomes of one or more subjects affected by the disease or condition but absent or present at lower frequency in subjects unaffected by the disease or condition according to step (c), in one or more subjects affected by the disease or condition, to identify a first set of one or more genetic variants; (e) sequencing the one or more copy number variants or one or more genome regions encompassing the one or more copy number variants determined to be statistically significant or present in the genomes of one or more subjects affected by the disease or condition but absent or present at lower frequency in subjects unaffected by the disease or condition according to step (c), in at least 100 subjects unaffected by the disease or condition, to identify a second set of one or more genetic variants; (f) determining a statistical significance of the first set of one or more genetic variants by comparing the sequencing information of step (d) to the sequencing information of step (e).

INCORPORATION BY REFERENCE

All publications, patents, and patent applications mentioned in this specification are herein incorporated by reference to the same extent as if each individual publication, patent, or patent application was specifically and individually indicated to be incorporated by reference in its entirety.

BRIEF DESCRIPTION OF THE DRAWINGS

The novel features of the invention are set forth with particularity in the appended claims. A better understanding of the features and advantages of the present invention can be obtained by reference to the following detailed description that sets forth illustrative embodiments, in which the principles of the invention are utilized, and the accompanying drawings of which:

FIG. 1 illustrates New Genome Biology and Disease Theory Concepts. FIG. 1 provides an overview of recent findings in genome biology and new disease theories that significantly impact the fields of disease and genetic research, drug discovery and therapeutics development, diagnostics development, and delivery of personalized medicine.

FIG. 3 illustrates the Impact of Genetic Variants. Examples of how DNA variants (SNPs/SNVs, InDels, CNVs, etc.) can alter gene structure and/or expression level, and thus, in many cases protein structure and/or expression level. Note, in some cases, a genetic variant may cause dysregulation in multiple cellular pathways (e.g., a transcription factor is impaired or its DNA binding site abolished). Interestingly, even synonymous SNVs have been found to impact protein structure via aberrant folding from rare codon usage, resulting in altered drug binding (Kimchi-Sarfaty C. et al., 2007 Science. 315 (5811):525-8).

DETAILED DESCRIPTION OF THE INVENTION & EXAMPLES

Definitions

Figure 2:
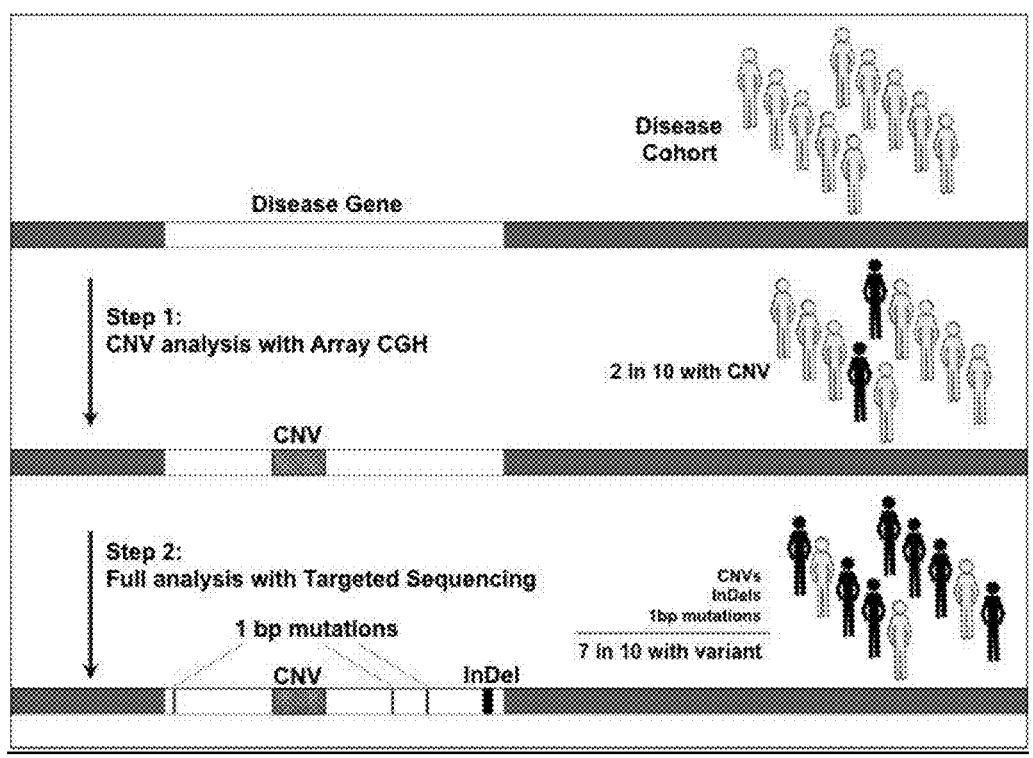
FIG. 2 illustrates The CNV Beacon Method. Copy number variants (CNVs) are used as a means to efficiently discover disease genes. A genome-wide copy number detection method, such as Array CGH, is used in Step 1 to ascertain the set of CNVs occurring at higher frequencies in a disease cohort but never or at very low frequencies in a normal (unaffected) cohort via CNV interpretation with the Normal Variation Engine (NVE). Once the CNV Beacon "lights up" the disease region (which may or may not contain one or more genes or regulatory elements), in Step 2, components within the CNV beacon (gene(s), regulatory and/or conserved elements) are sequenced in the affected and normal cohorts to determine the full extent of genetic variation in both, which enables sifting out pathogenic variants from benign variants in the affected cohort. In the example shown, the disease gene was flagged by a CNV present in 2 of 10 individuals with the disease. Sequencing analysis revealed 5 more affected individuals with a pathogenic mutation (1 with an Indel, 2 with uniquely occurring single base mutations, and 2 with the same single base mutation). Via the CNV Beacon, 20% of the affected tested were found with the CNV mutation (Beacon) and via subsequent targeted sequencing, 70% were found to have a mutation. For simplicity, the normal cohort is not depicted, but the CNV Beacon method also involves performing array CGH (CNV detection) and targeted sequencing (all variant types) of the normal cohort in order to discern pathogenic from benign variants in the disease cohort.

Affected—As used herein, refers to one or more individuals or organisms that have a disease, condition, or other observable biological phenomenon that is under study. Examples usage of the term includes, but is not limited to, "affected subject," "affected individual," "affected organism," "affected cohort," "affected group," and "affected population."

Array—As used herein, means an orderly arrangement of elements, to each of which has been assigned an address and an ID. In molecular biology, the term "array" is typically used to refer to arrangements of DNA, RNA, proteins, oligonucleotides, aptamers, or tissues.

Array-Based Comparative Genomic Hybridization (array CGH or aCGH)—The use of arrays for the simultaneous interrogation of thousands/millions of DNA sequences, whose genomic location is known. Comparison is between a 'control' and a test sample. aCGH is not limited to any particular array platform but is often considered synonymous with genomic arrays based on the historical use of bacterial artificial chromosomes (BACs—BAC arrays). In one nonexclusive meaning, aCGH is different from the majority of array analysis performed, namely that based on the comparison between expressions of genes in different tissues/individuals. The use of genomic DNA in aCGH results in data that has a simplistic structure, as each genomic segment can only be present in a discrete number of copies (usually 0, 1, 2, 3 or 4), whereas the expression levels of genes can vary from close to 0 to many million-fold. Some embodiments of aCGH use oligonucleotides of ~60 nucleotides in length adhered to the array via in situ synthesis methods.

Bacterial Artificial Chromosomes (BACs)—As used herein, vectors that allow for the isolation of genomic DNA segments of approximately 150,000 bp in size. BACs are used in human and mouse genome sequencing projects. Previous public sequencing projects were based on the sequencing of the complete inserts of BACs at high redundancy. DNA obtained from BACs whose genomic address is known, can be used to synthesize BAC arrays, whose performance in the detection of copy number abnormalities is highly robust. Moreover, BACs reporting a variant can immediately be queried on publicly available databases in order to obtain genomic location and gene content information.

Benign—As used herein, means something of little or no effect. For example, genetic variants can be pathogenic or benign. A "benign variant" or "benign genetic variant" is one that has little or no effect in a disease or condition, such as eye or hair color; that is, they are considered part of the normal biology of an individual or organism and thus are often referred to as "normal variants". Benign variants can also be considered as the opposite of "pathogenic variants," which are causal of a disease or condition. In some embodiments of the invention, it may be desirable to identify benign variants associated with a particular phenotype that do not cause disease. Such benign variants can be identified with the present invention by use of cohorts affected and unaffected by the phenotype or trait of interest such as a desirable growth characteristic in a plant crop or a particular size or coat color of a companion animal.

Biomarker—As used herein, means a characteristic that is objectively measured and evaluated as an indicator of normal biologic processes, pathogenic processes, or pharmacologic responses to a therapeutic intervention (Clin Pharmacol Ther. (2001) 69:89, Biomarkers Definitions Working Group). As used herein, one type of biomarker is a genetic variant, of any size or type, contained within an individual's genome that is associated with a disease or condition, such as drug response. Genetic variants found almost exclusively within an affected cohort, but never or almost never in an unaffected cohort, are characterized as candidate "causative biomarkers" or "causative mutations." Candidate causative biomarkers or mutations can be classified as causal of disease or a condition by a variety of methods. For example, in the case of a genetic variant that occurs within a gene, experiments can be performed verifying that the genetic variant causes a change in the protein product of the gene or the mutation can be introduced into the homologous gene of a model organism, which then results in a similar disease phenotype as observed in humans.

Breakpoint Mapping—As used herein, means the characterization of the molecular boundaries of any translocation/deletion/duplication/inversion. The information obtained from the molecular analysis of a given lesion (deletion, for example) allows for the creation of an assay for detection of that lesion. In one nonexclusive example, the molecular boundaries of a common microdeletion at a particular locus is isolated and the information used to generate a PCR-based assay that is capable of interrogating the genomes of individuals very rapidly.

Causative Mutation—As used herein, means a genetic variant characterized as causing a disease or condition. Causative mutations are also called causative biomarkers, as they can be objectively measured and used as indicators of a pathogenic process or condition, such as drug response. Examples of genetic variants include but are not limited to point mutations (e.g., deletions, additions, duplications, transitions, or transversions), chromosomal mutations (e.g., duplications, deletions, inversions, or translocations) or aberrations in ploidy (e.g., aneuploidy)

Common variant—As used herein, means a common variant is a genetic variant of any size or type that is typically present in a cohort or population at a frequency level of $>\sim 5\%$.

Condition—As used herein, means an observable characteristic in a human subject or non-human organism. The term condition can encompass disease states but is also used to describe other biological phenomena, such as adverse or poor drug response, height and weight and other visually observable physical characteristics, blood pressure or glucose level, or behaviors.

Copy Number Analysis—As used herein, means detection of the number of copies of a given genomic segment by interrogation of whole genomes or a subset of regions in genomes in a single experiment. For human and non-human animal genomes, this is of relevance to the creation of normal variation Knowledge Management Tools, and also of ascertaining correlations between certain disease states and the presence of dosage imbalances. Examples include a decrease in copy number from 2 to 1 in the case of a heterozygous deletion and an increase from 2 to 3 in the case of a heterozygous duplication.

Copy Number Variant (CNV)—See Dosage Polymorphism definition. CNVs can be present at any frequency level in the population and can be benign (no deleterious impact on normal biology) or pathogenic (disease causing).

Disease—As used herein, means a deviation from or interruption of the normal structure or function of any body part, organ, or system that is manifested by a characteristic set of symptoms and signs and whose etiology, pathology, and prognosis can be known or unknown. As used herein, the term "disease" is often used interchangeably with "disorder."

Dosage Polymorphism—(Copy number polymorphism)—As used herein, means the presence in a population of a genomic variant defined by an abnormal copy number (the normal copy number in humans is 2 for most chromosomes). Formally, a polymorphism includes occurrences in at least 1% of the population but this definition has been relaxed in the case of human genomic/genetic variation so that variants that are believed to be 'benign' but which still occur less often than 1% are still termed polymorphisms. A more accurate term is 'variant' or 'copy number variant', as this does not imply a given minimum frequency.

Drug rescue—The term "rescue" or "drug rescue" as used herein means identification of individual genetic variations, which can explain the differences in the response of subjects to drugs in clinical trials. In addition, some drugs show unexpected toxicity after several months on the market. These rare adverse events, not previously reported in the pre-marketing trials, can jeopardize the drug's success and decrease its market share. The present invention's platform allows a clinician or medical professional to quickly examine copy number variants in a particular patient and determine whether such variants are occurring within or overlapping genes associated with the drug's pathway or mechanism of action and search for the genetic variations, of any size or class, associated with the particular adverse events. Thus, "rescue" or "drug rescue" involves identification of genetic variations that cause differences in drug response. This information is then used to define a subset of the population for which the drug should not be prescribed and a screening test, often termed a companion diagnostic test, identifying these patients is developed. This information can also be used to redefine the lead compound, allowing for a better understanding of its potential effects. Therefore, the present invention's platform enables pharmacogenomics platforms with optimized and automatic data mining capabilities, high throughput genotyping, statistical and bioinformatics analysis, and target validation.

Drug response—The term "drug response" as used herein, means any biological response in an organism that is the result of exposure to the drug. Drug responses can be favorable, such as when a patient's disease is eradicated by treatment with the drug, or unfavorable, such as when a patient enters a coma upon treatment with a drug.

Epigenetic state or Epigenetic phenomena, as used herein, means changes produced in gene expression caused by mechanisms other than changes in the underlying DNA sequence. For example, methylation of cytosines (Cs) or histone modifications can affect expression of a gene. These molecular modifications of the DNA are often called "epigenetic marks." For example, increased or decreased methylation of Cs in a genome are part of normal biology but can also be associated with disease. As used herein, "epigenetic state" refers to a gene or region in a genome that reflects particular epigenetic phenomena. For example, in a particular disease cohort, a gene can be found that causes disease through multiple mechanisms, including, but not limited to, impairment of protein function by a SNV, deletion of the gene via a CNV, little or no expression of the gene due to a change in the epigenetic state of the gene itself and/or regulatory region(s) in the genome controlling expression of the gene.

Fluorescence In Situ Hybridization (FISH)—As used herein, means a method for visualizing a given sequence in the context of chromosomal position. Briefly, DNA is labeled with fluorescent dyes and hybridized to a set of immobilized chromosomes from an individual of interest. Each sequence is detected as localized fluorescence at the relevant genomic location. FISH is useful for detecting/validating suspected copy number changes (e.g., in a heterozygous deletion, a spot will likely be seen on only one of the two chromosome homologues).

Genetic variant or genetic variation—As used herein, means any difference at the genetic level between the genomes of two or more individuals or organisms. Types of genetic variants include, but are not limited to, single base changes (SNPs and SNVs), small insertions or deletions (indels), inversions, translocations, and copy number variants. Genetic variants vary in size from 1 base pair to several million base pairs, or even at the whole chromosome level such as is often the case in Down syndrome where there are three copies of chromosome 21.

Haplotype—As used herein, means a set of closely linked alleles (genes/DNA polymorphisms/SNPs) inherited as a unit. It is not trivial to deduce a haplotype from genotype information, which usually reports nothing about which chromosome a given variant is on. For example, if an individual is Aa at a given locus and Bb at another, the relevant haplotypes can either be AB/ab or Ab/Ba.

Individual—As used herein, means a person or subject. Individuals can be considered normal, apparently healthy, affected by a disease or condition, or unaffected by a disease or condition.

Karyotype—As used herein, means a description of the content and structure of the chromosomes in a given cell type. This analysis, which relies on direct light microscope visualization of the chromosomes, has been the mainstay of 'whole-genome' analysis in the past 50 years but suffers from a lack of resolution in that changes larger than 10-20 million base pairs are required before a variant is detected. While likely to be superseded at many levels by aCGH, karyotyping can still be necessary to detect translocations and inversions, which can be copy number neutral and, therefore, not detectable by aCGH.

Knowledge Management Tool (KMT)—As used herein, and referenced in U.S. Pat. No. 7,702,468, a KMT contains information on the frequencies of copy number variants in a normal cohort or population. As used herein, the Knowledge Management Tool (KMT) can be a component of the Normal Variation Engine (NVE) or interchangeably used with the term "Normal Variation Engine" ("NVE"). It is expected that the KMT, while intended to comprise frequency information on CNVs occurring in a normal cohort or normal population, will occasionally be tainted with CNVs present at a higher frequency in a cohort or population with a particular disease or condition. However, in these cases, the usefulness of the KMT is typically not diminished as the normal/unaffected cohorts or populations are generally larger than the affected cohort or population under study. Further, the enrichment of disease-causing or condition-causing CNVs in the affected (selected) cohort or population relative to an unaffected (unselected) cohort or population still enables identification of potentially disease-causing CNVs despite use of tainted KMTs. It will also be appreciated by those skilled in the art that a KMT can also contain frequency information on other types of genetic variants, such as, but not limited to, those identified in normal or unaffected cohorts via whole genome, exome-focused, or targeted sequencing studies of genomes, such that it enables interpretation of variants found in an affected cohort as benign or pathogenic.

Normal—As used herein, is term used to describe what is standard or the usual state. As applied in biology and medicine, a "normal state" or "normal person" is what is usual or most commonly observed. For example, individuals with disease are not typically considered normal. Example usage of the term includes, but is not limited to, "normal subject," "normal individual," "normal organism," "normal cohort," "normal group," and "normal population." In some cases, the term "apparently healthy" is used to describe a "normal" individual. Thus, an individual that is normal as a child may not be normal as an adult if they later develop, for example, cancer, Alzheimer's disease or are exposed to health-impairing environmental factors such as toxins or radiation. Conversely, a child treated and cured of leukemia can grow up to be an apparently healthy adult. Normal can also be described more broadly as the state not under study. For example, and as used herein, a normal cohort, used in conjunction with a particular disease cohort under investigation, includes individuals without the disease being studied but can also include individuals that have another unrelated disease or condition. Further, a normal group, normal cohort, or normal population can consist of individuals of the same ethnicity or multiple ethnicities, or likewise, same age or multiple ages, all male, all female, male and female, or any number of demographic variables. As used herein, the term "normals" can mean "normal subjects" or "normal individuals."

Normal variation—As used herein, "normal variation" is a term describing the spectrum of copy number variation, or frequencies of copy number variants, found in a normal cohort or normal population (see "Normal" definition). Normal variation can also refer to the spectrum of variation, or frequencies of variants, found in a normal cohort or normal population for any class of variant found in genomes, such as, but not limited to, single nucleotide variants, insertions, deletions, and inversions.

Normal Variation Engine (NVE)—As used herein, means a causative biomarker discovery platform, which includes, but is not limited to, a Knowledge Management Tool (KMT) containing information on the frequencies of CNVs in a normal cohort or population, that enables interpretation of CNVs found in an affected cohort as benign or pathogenic. Additional components of the NVE include, but are not limited to, methods and systems that enable identification and validation of causative genetic variants (biomarkers) of any size and type and a biorepository containing genomic DNA from normal subjects for use in validation studies and diagnostic test development. As used herein, the term "Normal Variation Engine" ("NVE") can be interchangeably used with the term "Knowledge Management Tool" ("KMT").

Odds Ratio (OR)—As used herein, means statistical measure often used in medical research as a metric of causality. For example, in genetic disease research it can be used to convey the significance of a variant in a disease cohort relative to an unaffected/normal cohort.

Pathogenic—As used herein, is generally defined as able to cause or produce disease. For example, genetic variants can be pathogenic or benign. In some cases, the term "pathogenic variant" or "pathogenic genetic variant" is more broadly used for a variant associated with or causative of a condition, which may or may not be a disease. In some cases, a pathogenic variant can be considered a causative variant or causative mutation, in which case the variant is causal of the disease or condition. Pathogenic variants can also be considered as the opposite of "benign variants," which are not causal of a disease or condition.

RNA variant—As used herein, means any type of RNA molecule produced from an organism's genome. Common examples include messenger RNA (mRNA), ribosomal RNA (rRNA), and transfer RNA (tRNA). Non-coding RNA (ncRNA) molecules, which are functional RNA molecules that are typically not translated into proteins, include but are not limited to, microRNAs, which can regulate gene expression by binding to an mRNA molecule and, through its inhibition or destruction, block its translation into protein. RNA variants also include the myriad of alternatively spliced variants that can be produced from a gene, which can be normal or aberrant. Aberrant splicing is often a cause of disease but the production of multiple normal variants from a single gene is a common regulatory mechanism for producing a set of proteins with altered structure and/or function.

Rare variant—As used herein means, a rare variant is a genetic variant of any size or type that is typically present in a cohort or population at a frequency level of about 0.1-3%, but can also be present at <0.1% and still have clinical relevance or usefulness as a biomarker of a disease or condition.

Single Nucleotide Polymorphism (SNP)—As used herein, means the most basic unit of variation at the level of DNA sequence. SNP includes variants in the nature of a single base—for example, at a given position, some individuals can have a 'G', while others can have a 'C'. Many of these changes are considered neutral while others can affect predisposition to certain disease states. Many SNPs are present in far less than 1% of the population, by some definitions used in the genetic community. The definition used for the NIH-sponsored dbSNP is "The Single Nucleotide Polymorphism database (dbSNP) is a public-domain archive for a broad collection of simple genetic polymorphisms. This collection of polymorphisms includes single-base nucleotide substitutions (also known as single nucleotide polymorphisms or SNPs), small-scale multi-base deletions or insertions (also called deletion insertion polymorphisms or DIPs), and retroposable element insertions and microsatellite repeat variations (also called short tandem repeats or STRs). Please note that in this chapter, you can substitute any class of variation for the term SNP." (www.ncbi.nlm.nih.gov/bookshelf/br.fcgi?book=handbook&part=ch5):

Single Nucleotide Variant (SNV)—See Single Nucleotide Polymorphism definition. SNVs can be present at any frequency level in the population and can be benign (no deleterious impact on normal biology) or pathogenic (disease causing). Because the classical definition of a SNP is that it is present at ≥1% frequency in a population, in some cases SNPs are considered to be a sub-class of SNVs.

Subject—As used herein, means an entity from whom genomic DNA is obtained for genome analysis by one or more methods described herein so as to obtain copy number variant data, genetic variant data (any size or type), or epigenetic data (e.g., assaying if cytosines are methylated). Thus, a subject can be one individual from at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 individuals utilized to compile said data (or data set) for one or more cohorts, wherein a cohort represents an ethnic group, a patient group, a patient group associated with a particular condition, disease or disorder, a group or subgroup of individuals from a clinical trial or associated with a particular response to a treatment regimen. A subject can also be one individual from at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100, 000, 200,000, 500,000, 700,000, or 1,000,000 individuals utilized to compile said data (or data set) for one or more cohorts, wherein a cohort represents subjects unaffected by a particular condition, disease or disorder, a group or subgroup of individuals from a clinical trial or unaffected by a particular response to a treatment regimen. In addition, a subject can mean a test subject, a patient or a candidate for a therapeutic, where genomic DNA from said subject, patient, or candidate is obtained for genome analysis by one or more methods of the present invention herein, so as to obtain copy number variant data, genetic variant data (any size or type), or epigenetic data (e.g., assaying if cytosines are methylated) in said subject, patient or candidate. A subject can be a human, a non-human animal (e.g., a cat, dog, pig, mouse, rat, cow, or horse) or a plant.

Unaffected—As used herein, refers to one or more individuals or organisms that do not have a disease, condition, or other observable biological phenomenon that is under study. Example usage of the term includes, but is not limited to, "unaffected subject," "unaffected individual," "unaffected organism," "unaffected cohort," "unaffected group," and "unaffected population." In some cases, the term "normal" is used to mean "unaffected."

Copy Number Variation (CNV) Beacon Method for Discovery of Causative Biomarkers/Mutations In one embodiment the Copy Number Variation Beacon (CNV Beacon) method can be used, as described herein, to find causative genetic mutations of common, complex diseases and causative biomarkers of disease and drug response. In one embodiment, the CNV Beacon method is used for identification of rare variants that cause disease or a condition such as drug response. Rare variants, typically present in the population at large at 0.1% to 2-3% frequency, can cause disease, including common diseases (Bodmer W. and Bonilla C. Nat Genet. 2008; 40(6):695-701). In another embodiment, the CNV Beacon method can be used for identification of common variants, typically >5% frequency in the population at large, that cause disease or a condition such as drug response. Thus, the CNV Beacon method is broadly applicable for the discovery of genes or genomic loci for diseases or conditions that have a genetic component in their etiology via the identification of both rare and common genetic variants. Copy number variation can be analyzed using one or more of the methods disclosed in U.S. Ser. No. 12/449,566, filed May 3, 2007, which is herein incorporated by reference in its entirety.

The methods herein can be employed to find genes/loci/biomarkers causative of complex diseases including but not limited to cancer, heart disease, diabetes, autism, Parkinson's disease, Alzheimer's disease, schizophrenia, and bipolar disorder. For example, as applied to autism, the method can result in the discovery and validation of autism mutations in genes. It should be appreciated by those skilled in the art that finding causative mutations for most diseases is more challenging than previously thought due to recent findings in genome biology and new theories on the genetic causes of diseases (see FIG. 1 for an overview of these factors). A critical barrier to solving complex diseases is finding the multiple genetic causes resulting in a common phenotype. In other words, a disease that is diagnosed via a common set of symptoms in patients may actually be two or more different diseases caused by mutations in genes that are unrelated (i.e., a common disease is actually an amalgam of rare diseases that have not been genetically resolved). Further, it can be appreciated by those skilled in the art that disease heterogeneity and severity may result not only from different genes, but also different mutations within each disease-causing gene. Thus, current one-size-fits-all therapies will in many cases be replaced by multiple therapy choices, with therapy selection dependent on the genotype(s) of the patient, which can be ascertained via a diagnostic test (e.g., companion diagnostic genetic test) prior to administration of the appropriate therapy. In some cases, early detection tests, administered before disease onset/occurrence (e.g., in newborns), may enable prevention or delay of disease onset by administration of therapies before symptoms appear in the patient. Most complex diseases are 50-90% heritability yet only 1-10% of genetic causes are known. Further, key environmental factors cannot be adequately ascertained without understanding if environmentally responsive genes are involved, or not, in disease onset and progression. Thus, methods of the invention described herein can fill the urgent need to identify the genetic causes of disease and also yield genetic biomarkers that facilitate the development of novel diagnostic and therapeutic personalized medicine products, which will enable delivery of safer, more effective, and lower cost healthcare to patients. However, one of the biggest challenges to finding disease-causing variants is that the vast majority of variants are not pathogenic but are benign. The present invention greatly accelerates uncovering pathogenic variants and much lower cost than other genome-wide analysis methods.

The genome analysis tools and experimental design used in the CNV Beacon method for discovery of causative mutations are illustrated in FIG. 2. Once a CNV identifies a gene (or regulatory site) as potentially causative of disease, the CNV-containing gene can then be sequenced to identify the full set of mutations that cause the disease. Since benign (normal) variants outnumber pathogenic variants, the frequency of variants found must be ascertained in both the affected and normal cohorts to establish with high confidence that a variant causes disease. In step 1, CNVs are detected genome-wide using a method such as array CGH, single nucleotide polymorphism microarrays (SNP arrays), sequencing, or even fluorescence in situ hybridization (FISH). An analysis is then performed by comparing disease cohort CNVs to the comprehensive set of normal (benign) CNVs present in a Normal Variation Engine (NVE), also known as the Knowledge Management Tool (KMT) described in U.S. Pat. No. 7,702,468, which is herein incorporated by reference in its entirety. The NVE can comprise genome-wide CNVs representative of the population at large or of a particular subpopulation (e.g., when investigating a disease known to occur at higher prevalence in a particular ethnic group). In one embodiment, a NVE is created up front and then used to interpret data from any disease or drug response cohort. This is a rapid process that yields a set of candidate disease genes or regions for targeted sequencing (step 2) in the affected and normal cohorts. The statistical and experimental criteria for distilling disease-causing variants from normal variants found in both steps 1 and 2 include, but are not limited to, odds ratio calculations, bioinformatics analysis of genetic variants to predict if they are deleterious or benign, validation of CNVs with solution-based assays or sequencing, and replication of findings in additional cohorts of affected and unaffected individuals.

In one embodiment information and/or data are acquired from normal subjects not at risk of or afflicted/diagnosed with a particular disease or condition. In another embodiment information and/or data are acquired from subjects at risk of or afflicted/diagnosed with a particular disease or condition. In one embodiment information and/or data is acquired from at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 or more normal subjects. In another embodiment information and/or data is acquired from at least at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 or more subjects at risk of or afflicted/diagnosed with a particular disease or condition. In another embodiment information and/or data can be compiled from about 100 to 1,000,000, 1,000 to 1,000,000, 10,000 to 1,000,000, or 100,000 to 1,000,000 subjects. In some embodiments, a very rare or private mutation may be the cause of the patient's disease or condition and thus even one individual's genome may be interpretable with an NVE that contains CNV and/or other variant data on a large number of normal individuals. For example, a G2019S mutation in the protein product of the LRRK2 gene causes a particular subtype of Parkinson's disease in ~1% of Parkinson's cases (Orzelius L. N Engl J. Med. 2006 Jan. 26; 354(4):424-5), and can range higher in some ethnic groups. A single patient with the disease may be found, upon genome-wide detection of CNVs with aCGH of this patient's genome, to have a very rare CNV within or near the LRRK2 gene that is causative of the patient's Parkinson's disease. This single CNV, which may be a de novo mutation, in one patient may be interpretable as pathogenic with an NVE containing CNV frequency data on 100 or more normal subjects.

In one embodiment whole genome analysis of CNVs with microarrays, such as CGH and SNP arrays, is generally less expensive, more accurate, and faster than whole genome sequencing. The total level, meaning total number of variants, of variation for CNVs in human genomes is considerably lower than it is for SNVs queried by whole genome sequencing. With CNVs, there are far fewer genetic variants to compare. The discovery power of detecting CNVs—rather than sequencing all 3 billion bases of the human genome—is highlighted in Table 1. In effect, use of CNVs significantly reduces the genetic variation "search space," as indicated by the difference in search space between CNVs vs. SNVs when estimated both at the population level and individual level (Table 1). In one preferred embodiment of the CNV Beacon method, rare causative genetics variants can be found using array CGH, or other whole genome CNV detection method such as SNP genotyping microarrays, followed by targeted sequencing, which takes advantage of the reduced variation search space afforded by CNVs. Whereas, with whole genome sequencing, as well as with whole-exome sequencing, a very large search space must be queried using very large cohorts (disease and normal) and significantly greater informatics and bioinformatics resources to find causal variants.

be done using induced pluripotent stem cells (iPSCs) generated from one or more subjects affected by a disease or condition in which one or more pathogenic variants is present in a given subject's genome (Schule B. et al. 2009, Biochim Biophys Acta. 1792(11):1043-51; Saha K. and Jaenisch R. 2009, Cell Stem Cell. 5(6):584-95).

The CNV Beacon method is also applicable and informative in the context of the smaller number but larger footprint of CNVs in the genome. Via a smaller search space enriched with variants that have a higher probability to alter a gene's structure or expression level, CNVs are an effective rare variant discovery shortcut. Since the search space for CNVs is smaller, the methodology benefits by requiring much smaller cohort sizes, affected and unaffected, for disease gene discovery.

In some cases, a disease or condition (e.g. drug response) is caused by a gene/locus containing only SNVs and/or small insertion/deletions (indels). In some embodiment this would not be detected by array CGH. Therefore, to estimate the proportion of disease genes that the CNV Beacon method could theoretically miss, the Human Genome Mutation Database (HGMD) was surveyed to determine how many CNVs>5 Kb in size (the approximate resolution in some embodiments of whole-genome array CGH platforms) are present in already known genes causative of disease. A summary of this survey is presented in Tables 2 and 3 to emphasize that numerous genes causative of single gene (Mendelian) and multiple gene (complex) disorders would have been found using the NVE and CNV Beacon method. With current array CGH platforms, it is likely that rare CNVs will be found in a subset of the affected cohort for a majority of disease-causing genes and sequencing these genes will uncover the additional smaller rare variants causing the disease in the remainder of the affected cohort. For example, a reasonable scenario for a complex disease and what can be detected is as follows:

TABLE 1

Estimation of Reduction in Genetic Variation in Search Space

| Variation Level | CNVs | SNVs | Fold Difference | Source |
|---|---|---|---|---|
| Population | ~12,000 >5% frequency | ~11,000,000 >1% frequency | 1,000x | Frazer K et al. Nat Rev Genet. 2009 April; 10(4): 241-51. Conrad D et al. Nature. 2010 Apr. 1; 464(7289): 704-12. |
| Individual | 234 | 3,420,306 | 15,000x | Lupski J et al. N Engl J Med. 2010 Apr. 1; 362(13): 1181-91. |

In another embodiment the present invention provides reduced variation search space (i.e., less variants to interpret in an affected cohort relative to those present in an unaffected cohort) via use of CNVs. In another embodiment the odds of a CNV having a deleterious effect on a gene or regulatory locus are greater due to their larger size relative to SNVs and InDels. In some embodiments this can produce a search space that is not only smaller, but it is potentially enriched in variants more likely to cause a disease or condition. For example, the CNV detection method in one embodiment of array CGH can identify CNVs ~3,000 bp in size or larger, which can impact a third or more of the average size gene (~10,000 bp). In contrast, an SNV alters only 1 of the 10,000 bp of an average size gene, which can result in an inactive protein (e.g., nonsynonymous and missense) but the majority of 1 bp changes will likely be benign or difficult to interpret (e.g., synonymous, intronic, and promoter/enhancer SNVs). See FIG. 3, which discloses how genetic variants can alter structure and/or expression level of a gene product. It can be appreciated by those skilled in the art that functional validation of genetic variants such as those described in FIG. 3 may Disease cohort is tested with array CGH with a patient number of: 1,000

20 genes cause the disease at 5% each, so number of patients for a given gene is: 50

Each gene has a set of mutations with CNVs causing 10%, so number of patients with a CNV is: 5.

In order to determine the relevance of finding only 5 CNVs (i.e., rare variants present in only 0.5% of the affected cohort) in each candidate disease gene, a metric of causality, the Odds Ratio (OR), can be used. OR values can be used in genetic research to convey the significance of a variant in a disease cohort relative to an unaffected/normal cohort. Thus, assuming the potentially disease-causing CNVs are absent or found only once in a normal cohort of 3,000 individuals (if 0 are found, a value of 1 is typically assumed in the calculation), the OR value for the CNVs on a per gene basis is:

$$[5/(1,000-5)]/[1/(3,000-1)]=15.1$$

If only 2 patients are found with the CNV, the OR is:

$$[2/(1,000-2)]/[1/(3,000-1)]=6.0$$

If 5 patients are found with the CNV but so are 5 normals, the OR is:

[5/(1,000−5)]/[5/(3,000−5)]=3.0

Thus, even with less favorable odds in the number of CNVs detected in the affected and normal cohorts, the Tier 1 discovery study (Step 1 using whole-genome array CGH) will likely reveal the candidate disease genes via the CNV Beacons. In contrast, SNP genome-wide association studies (GWAS), which are designed to detect common variants associated with a disease, rarely yield ORs >1.5 for the tag SNPs (a SNP that may "tag" a genomic region of interest but is not usually causative of the disease or condition under study) and the 10-100 Kb disease-associated loci that are found may or may not contain the causal variant/gene. With the CNV Beacon approach, the CNVs identified via use of the NVE are often themselves found to be causative. Thus, winnowing the candidate disease gene list, generated from Step 1 of the CNV Beacon method, down to a set of causative disease genes and the full set of mutations contained within them can be rapidly and cost-effectively accomplished by the targeted sequencing of the candidate disease genes. This is in sharp contrast to the main sequencing options, exomes and genomes, used for rare variant discovery, which can use 100-1,000-fold more sequencing work at the gene level (assuming for the CNV Beacon method that 20-200 candidate genes of the ~20,000 genes total in human genomes are sequenced), not including the costs and complexity of analysis for the many fold more variants found with these methods. Further, in silico and functional validation studies of the disease genes/mutations, as well as replication of the identified variants in additional cohorts of affecteds and unaffecteds, are additional components of the disease biomarker discovery and validation process.

TABLE 2

Large CNVs (>5 Kb) Present in Single Gene Diseases
Single Gene Disorder Examples

| Disease | Gene | Total Mutations | >5 Kb Mutations | % Large CNVs |
|---|---|---|---|---|
| Hemophilia A | F8 | 1305 | 88 | 6.7% |
| Cystic fibrosis | CFTR | 1273 | 27 | 2.1% |
| Muscular dystrophy | DMD | 916 | 514 | 56.1% |
| Hemophilia B | F9 | 867 | 40 | 4.6% |
| Neurofibromatosis | NF1 | 837 | 62 | 7.4% |
| Phenylketonuria | PAH | 537 | 10 | 1.9% |
| Beta thalassemia, sickle cell anemia, etc. | HBB | 462 | 28 | 6.1% |
| Polycystic kidney disease | PKD1 | 292 | 4 | 1.4% |
| Neurofibromatosis | NF2 | 270 | 29 | 10.7% |
| Tay-Sachs | HEXA | 122 | 1 | 0.8% |
| Canavan disease | ASPA | 70 | 4 | 5.7% |
| Charcot-Marie-Tooth | PMP22 | 63 | 5 | 7.9% |
| Average | | | | 9.3% |
| Average, excluding DMD | | | | 5% |

Mutation statistics from: www.hgmd.cf.ac.uk (updated through ~2006)

TABLE 3

Large CNVs (>5 Kb) Present in Multiple Gene Diseases
Common, Complex Disease Examples

| Disease | Gene[1] | Total Mutations | >5 Kb Mutations | % Large CNVs |
|---|---|---|---|---|
| Autism, mental retardation (Rett syndrome) | MECP2 | 391 | 40 | 10.2% |
| Autism, mental retardation | FMR1 (FRAXA) | 30 | 10 | 33.3% |
| Autism, mental retardation | CNTN4[2] | 2 | 1 | 50.0% |
| Breast cancer | BRCA1 | 938 | 59 | 6.3% |
| Beast cancer | BRCA2 | 700 | 15 | 2.1% |
| Alzheimer's disease | APP | 35 | 5 | 14.3% |
| Alzheimer's disease | PSEN1 | 179 | 2 | 1.1% |
| Alzheimer's disease | PSEN2 | 13 | 0 | 0.0% |
| Parkinson's disease | PARK2 | 146 | 35 | 24.0% |
| Parkinson's disease | PINK1 (PARK6) | 43 | 1 | 2.3% |
| Parkinson's disease | LRRK2 (PARK8) | 20 | 0 | 0.0% |
| Parkinson's disease | DJ1 (PARK7) | 17 | 2 | 11.8% |
| Parkinson's disease | SNCA (PARK1/PARK4) | 5 | 2 | 40.0% |
| Parkinson's disease | UCHL1 (PARK5) | 2 | 0 | 0.0% |

[1]Mutation statistics from: www.hgmd.cf.ac.uk (updated through ~2006)
[2]CNTN4 mutations from: Am J Hunn Genet. 2004 June; 74(6): 1286-93; J Med Genet. 2009 March; 46(3): 176-82

Methods for Evaluating Copy Number

A number of methods and products can be utilized in evaluating one or more copy number variants of a gene. These include, but are not limited to, PCR, array comparative genomic hybridization (aCGH), sequencing (such as high-throughput sequencing), single nucleotide polymorphism (SNP) genotyping, multiplex ligation-dependent probe amplification (MLPA), Invader assay, or fluorescence in situ hybridization.

In one embodiment, a PCR assay is used. In particular, PCR assays enable detection of precise boundaries of gene/chromosome variants, at the molecular level, and which boundaries are identical in different individuals. For example, the molecular boundaries of a microdeletion on chromosome 8 (present in 5% of all normal individuals) was sequenced in 100 individuals and is shown to have an identical sequence across the breakpoint. The PCR assay is based on the amplification of a junction fragment present only in individuals that carry this deletion. This assay converts the detection of a loss by array CGH to one of a gain by PCR.

Different DNA isolation and PCR techniques are known to those with skill in the art. Examples of PCR techniques that can be used in the present invention include, but are not limited to quantitative PCR, quantitative fluorescent PCR (QF-PCR), multiplex fluorescent PCR (MF-PCR), real time PCR (RT-PCR), single cell PCR, PCR-RFLP/RT-PCR-RFLP, digital PCR (dPCR), droplet digital PCR (ddPCR), reverse transcription PCR, single marker qPCR, hot start PCR and Nested PCR. Other suitable amplification methods include the ligase chain reaction (LCR), ligation mediated PCR (LM-PCR), degenerate oligonucleotide probe PCR (DOP-PCR), transcription amplification, self-sustained sequence replication, selective amplification of target polynucleotide sequences, isothermal amplification, linear amplification, isothermal linear amplification, SPIA, consensus sequence primed polymerase chain reaction (CP-PCR), arbitrarily primed polymerase chain reaction (AP-PCR) and nucleic acid based sequence amplification (NABSA).

PCR can be conducted using methods and reagents known in the art. For example, the PCR products can be directly sequenced bi-directionally by dye-terminator sequencing. PCR can be performed in a 384-well plate in a volume of 15 ul containing 5 ng genomic DNA, 2 mM MgCl2, 0.75 ul DMSO, 1 M Betaine, 0.2 mM dNTPs, 20 pmol primers, 0.2 ul AmpliTaq Gold (Applied Biosystems), 1× buffer (supplied with AmpliTaq Gold). Thermal cycling conditions are as follows: 95° C. for 10 minutes; 95° C. for 30 seconds, 60° C. for 30 seconds, 72° C. for 1 minute for 30 cycles; and 72° C. for 10 minutes. PCR products can be purified and optionally can be separated by capillary electrophoresis on an ABI13730 DNA Analyzer (Applied Biosystems).

In one embodiment, a PCR-based approach is real-time quantitative PCR (qPCR). Alternative methods for the simultaneous interrogation of multiple regions include quantitative multiplex PCR of short fluorescent fragments (QMPSF), multiplex amplifiable probe hybridization (MAPH) and multiplex ligation-dependent probe amplification (MLPA), in which copy-number differences for up to 40 regions can be scored in one experiment. Another approach is to specifically target regions that harbor known segmental duplications, which are often sites of copy-number variation. By targeting the variable nucleotides between two copies of a segmental duplication (called paralogous sequence variants) using a SNP-genotyping method that provides independent fluorescence intensities for the two alleles, it is possible to detect an increase in intensity of one allele compared with the other.

In another embodiment, the amplicons are bound to beads using the sequencing element of the nucleic acid tag under conditions that favor a single amplicon molecule to bind a different bead and amplification occurs on each bead. In some embodiments, such amplification occurs by PCR. Each bead can be placed in a separate well, which can be a (optionally addressable) picoliter-sized well. In some embodiments, each bead is captured within a droplet of a PCR-reaction-mixture-in-oil-emulsion and PCR amplification occurs within each droplet. The amplification on the bead results in each bead carrying at least one million, at least 5 million, or at least 10 million copies of the single amplicon molecule.

In embodiments where PCR occurs in oil-emulsion mixtures, the emulsion droplets are broken, the DNA is denatured and the beads carrying single-stranded nucleic acids clones are deposited into a well, such as a picoliter-sized well, for further analysis according to the methods described herein. These amplification methods allow for the analysis of genomic DNA regions. Methods for using bead amplification followed by fiber optics detection are described in Margulies M. et al. 2005, Nature. 15; 437(7057):376-80, and as well as in US Publication Application Nos. 20020012930; 20030068629; 20030100102; 20030148344; 20040248161; 20050079510, 20050124022; and 20060078909.

In another embodiment sequencing is used. Nucleic acid molecules (e.g., genomic DNA) can be sequenced utilizing sequencing methods that are conventional in the art. Sequencing can be accomplished through classic Sanger sequencing methods, which are known in the art. Sequence can also be accomplished using high-throughput systems some of which allow detection of a sequenced nucleotide immediately after or upon its incorporation into a growing strand, i.e., detection of sequence in substantially real time or real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read (or 500-1,000 bases per read for 454).

In some embodiments, high-throughput sequencing involves the use of technology available by Helicos BioSciences Corporation (Cambridge, Mass.) such as the Single Molecule Sequencing by Synthesis (SMSS) method. SMSS can allow for sequencing the entire human genome in up to 24 hours. This fast sequencing method also allows for detection of a SNP/nucleotide in a sequence in substantially real time or real time. Finally, SMSS is powerful because, like the MIP technology, it does not use a pre-amplification step prior to hybridization. SMSS does not use any amplification. SMSS is described, e.g., in US Patent Publication Application Nos. 20060024711; 20060024678; 20060012793; 20060012784; and 20050100932.

In one embodiment, high-throughput sequencing involves the use of technology available by 454 Lifesciences, Inc. (Branford, Conn.) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

In another embodiment, a PCR-amplified single-strand nucleic acid is hybridized to a primer and incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) are added sequentially. Each base incorporation is accompanied by release of pyrophosphate, which is converted to ATP by sulfurylase, which drives synthesis of oxyluciferin and the release of visible light. Since pyrophosphate release is equimolar with the number of incorporated bases, the light given off is proportional to the number of nucleotides adding in any one step. The process repeats until the entire sequence is determined. In one embodiment, pyrosequencing is utilized to analyze amplicons to determine whether breakpoints are present. In another embodiment, pyrosequencing also maps surrounding sequences as an internal quality control.

Pyrosequencing analysis methods are known in the art. Sequence analysis can include a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structured such that the identity of one of its positions is correlated with the identity of the fluorophore attached to that nonamer. To the extent that the ligase discriminates for complementarily at that queried position, the fluorescent signal allows the inference of the identity of the base. After performing the ligation and four-color imaging, the anchor primer: nonamer complexes are stripped and a new cycle begins. Methods to image sequence information after performing ligation are known in the art.

In another embodiment a sequencing technology that can be used is SOLEXA sequencing (Illumina) SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

In another embodiment a sequencing technology that can be used is the single molecule, real-time (SMRT™) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

In another embodiment a sequencing technology that can be used to determine the status of one or more molecular markers in a sample is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

In another embodiment a sequencing technique that can be used is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

In other embodiments sequencing techniques that can be used are a semiconductor sequencing methods commercialized by Ion Torrent Systems. Such methods are described, for example, in U.S. Patent Application Publication Nos. 20100197507, 20100188073, 20100137143, 20100035252, 20090127589, and 20090026082. Ion Torrent Systems technology can use chemical-sensitive field effect transistors (FETs). Ion Torrent Systems technology can include use of a semiconductor chip that comprises multiple layers, e.g., a layer with micro-machined wells, an ion-sensitive layer, and an ion sensor layer. Nucleic acids attached to beads can be introduced into the micro-machined wells. A clonal population of single nucleic acids can be attached to a single bead. One type of deoxyribonucleotide (e.g., dATP, dCTP, dGTP, or dTTP) can be introduced into the micro-machined wells to initiate sequencing of the nucleic acids on the beads. Upon incorporation of nucleotides by DNA polymerase, protons are released in the well which can be detected by the ion sensor. The semiconductor chip can then be washed and the process can be repeated with a different deoxyribonucleotide. A plurality of nucleic acids can be sequenced in the micro-machined wells of a semiconductor chip.

Another sequencing technique that can be used is DNA nanoball sequencing, e.g., as used by Complete Genomics. In DNA nanoball sequencing, DNA fragments are produced to a size of about 400 to 500 base pair. Adapter sequences are ligated to the fragments, and the fragments are circularized. The circular fragments are then copied using rolling circle replication. This amplification can result in a multitude of single-stranded copies of each fragment. The DNA copies can concatenate head to tail in a long strand and then be compacted into a "DNA nanoball" (DNB). A DNB can on average be approximately 200 nanometers in diameter. The DNA nanoball can be adsorbed onto a sequencing flow-cell (silicon chip). DNBs can be packed tightly on a silicon chip at "sticky spots." A sticky spot can be one of 2.8 billion spots in an area 25 mm wide by 75 mm long. On DNB can stick to one sticky spot. A silicon chip filled with DNBs can be referred to as a DNA nanoball array. Sequencing by ligation can be used to determine nucleic acid sequence. For example, a ligase-based DNA reading technology called combinatorial probe-anchor ligation (cPAL) can be used. cPAL technology can provide high accuracy reading of five-base sequences of DNA. Seven five base segments from each of the two ends of each DNA fragment can yield 70 bases from each fragment. Over 90% of a complete human genome can be reconstructed using 70 base reads from each fragment using software.

In another embodiment, whole genome array-based comparative genome hybridization (array CGH) analysis, or array CGH on a subset of genomic regions, can be used to efficiently interrogate human genomes for genomic imbalances at multiple loci within a single assay. The importance of normal copy number variation involving large segments of DNA has been unappreciated. Array CGH is a breakthrough technique in human genetics, which is attracting interest from clinicians working in fields as diverse as cancer and IVF (In Vitro Fertilization). The use of CGH microarrays in the clinic can be used to identify regions of genomic imbalance associated with disease. Advances from identifying chromosomal critical regions associated with specific phenotypes to identifying the specific dosage sensitive genes can provide therapeutic opportunities of benefit to patients. Array CGH is a specific, sensitive and rapid technique that enables the screening of the whole genome in a single test. It can facilitate and accelerate the diagnostic process in human genetics and can have a profound impact on the screening and counseling of patients with genetic disorders. The exact location on the chromosome where an aberration has occurred can be identified and these changes can be mapped directly onto the genomic sequence.

An array CGH approach provides a robust method for carrying out a genome-wide scan to find novel copy number variants (CNVs). Array CGH methods use labeled fragments from a genome of interest, which can be competitively hybridized with a second differentially labeled genome to arrays that are spotted with cloned DNA fragments, revealing copy-number differences between the two genomes. Genomic clones (for example, BACs), cDNAs, PCR products and oligonucleotides can all be used as array targets. The use of array CGH with BACs was one of the earliest employed methods and is popular, owing to the extensive coverage of the genome it provides, the availability of reliable mapping data and ready access to clones. The last of these factors plays a role in array experiments and confirmatory FISH experiments.

The use of CGH with arrays that comprise long oligonucleotides (e.g., 50-200 bp, 75-200 bp, 25-150 bp, 50-150 bp, or 60-100 bp) can improve the detection resolution (in one embodiment, as small as about 3-5 kb, 1-10 kb, 2-10 kb, 2-8 kb, 2-5 kb sized CNVs on arrays designed for interrogation of human whole genomes) over that achieved using BACs (limited to 50-100 kb or larger sized CNVs due to the large size of BAC clones). In some embodiments, the resolution of oligonucleotide CGH arrays is achieved via in situ synthesis of 1-2 million unique features/probes per microarray, which includes microarrays available from Roche NimbleGen and Agilent Technologies. An overview of array CGH methods is provided in Table 4.

Another method for copy number detection that uses oligonucleotides is representational oligonucleotide microarray analysis (ROMA). ROMA is similar to that applied in the use of BAC and oligo CGH arrays, but to increase the signal-to-noise ratio, the 'complexity' of the input DNA is reduced by a method called representation or whole-genome sampling. Here the DNA that is to be hybridized to the array is treated by restriction digestion and then ligated to adapters, which results in the PCR-based amplification of fragments in a specific size-range. As a result, the amplified DNA makes up a fraction of the entire genomic sequence—that is, it is a representation of the input DNA that has significantly reduced complexity, which leads to a reduction in background noise.

include (a) the generation of genome-wide clone resources integrated into the finished human genome sequence, (b) the development of high-throughput microarray platforms, and (c) the optimization of comparative genomic hybridization protocols and data analysis systems. Together, these developments have accumulated in a so-called 'molecular karyotyping' technology that allows the sensitive and specific detection of single copy number changes of submicroscopic chromosomal regions throughout the entire human genome.

Many of the basic procedures followed in microarray-based genome profiling are similar, if not identical, to those followed in expression profiling and SNP analysis, including the use of specialized microarray equipment and data-analysis tools. Microarray-based expression profiling has been well established in the last decade. Examples of the use of microarrays in nucleic acid analysis that can be used are described in U.S. Pat. No. 6,300,063, U.S. Pat. No. 5,837,832, U.S. Pat. No. 6,969,589, U.S. Pat. No. 6,040,138, U.S. Pat. No. 6,858,412, U.S. patent application Ser. No. 08/529,115, U.S. patent application Ser. No. 10/272,384, U.S. patent application Ser. No. 10/045,575, U.S. patent application Ser. No. 10/264,571 and U.S. patent application Ser. No. 10/264,574. It should be noted that there are also distinct differences such as target and probe complexity, stability of DNA over RNA, the presence of repetitive DNA and the need to identify single copy number alterations in genome profiling.

Sub-microscopic copy number alterations do not always have phenotypic consequences, as in some cases identical alterations were found in unaffected individuals. This notion has been substantiated by studies revealing the presence of LCVs (large copy number variations) in apparently normal individuals. In addition, once it has been established that a

TABLE 4

Comparison of CGH Platforms for CNV Detection

| CGH Platform | Array Design | Probes | Size | Resolution | per Person | Comments |
|---|---|---|---|---|---|---|
| BAC clones, spotted | whole genome | 19,000 | 150,000 bp | ~100,000 bp | 10 | Obsolete, most using oligo CGH or SNP arrays for CNV detection |
| Oligos, in situ synthesis | whole genome | 1-2 million | 50 bp | ~3,000 bp | 250 | Agilent 1M and NimbleGen 2.1M are top CGH platforms |
| Oligos, in situ synthesis | custom regions | variable | 50 bp | 10-100 bp | — | Useful for validating small-sized CNVs and fine-mapping CNV breakpoints |

In another embodiment an array-based approach that uses hybridization signal intensities that are obtained from the oligonucleotides, such as those employed on Affymetrix SNP arrays or in Illumina Bead Arrays. Here hybridization intensities are compared with average values that are derived from controls, such that deviations from these averages indicate a change in copy number. As well as providing information about copy number, SNP arrays have the added advantage of providing genotype information. For example, they can reveal loss of heterozygosity, which can provide supporting evidence for the presence of a deletion, or can indicate segmental uniparental disomy (which can recapitulate the effects of structural variation in some genomic regions—Prader-Willi and Angelman syndromes, for example).

Chromosome banding is one of the most widely used techniques in routine cytogenetics and has been invaluable in the search for chromosomal aberrations causally related to e.g., mental retardation and congenital malformation syndromes. Conceptual and technical developments in molecular cytogenetics are now enhancing the resolving power of conventional chromosome analysis techniques from the megabase to the kilobase level. Tools that have mediated these developments copy number alteration has occurred in a patient, it can be that this alteration has not been described before in the literature, posing serious problems for genetic counseling. However, in due time increasing numbers of these abnormalities will continue to be documented, either in individual case reports or in publicly available online databases, furthering our understanding of the genetic basis of these disorders. The KMTs/NVE used in the present invention also provide a compilation of information on normal copy number variations that permit an identification and analysis of those variations of significance.

The development of comparative genomic hybridization (CGH) (Kallioniemi A. et al., 1992, Science 258: 818-21) provided the first efficient approach to scanning entire genomes for variations in DNA copy number. In a typical CGH measurement, total genomic DNA is isolated from test and reference cell populations, differentially labeled, and hybridized to a representation of the genome that allows the binding of sequences at different genomic locations to be distinguished. More than two genomes can be compared simultaneously with suitable labels. Hybridization of highly repetitive sequences is typically suppressed by the inclusion of unlabeled Cot-1 DNA in the reaction. Metaphase chromosomes can be used for the representation of the genome and the location of copy number variations between test and reference genomic DNA can be mapped to the physical position on the chromosomes.

DNA microarrays can be used containing elements that are mapped directly to the genome sequence (Pinkel D. et al., 1998. Nat. Genet. 20:207-11). The relative hybridization intensity of test and reference signals at a given location can be proportional to the relative copy number of those sequences in the test and reference genomes. If the reference genome is normal then increases and decreases in signal intensity ratios directly indicate DNA copy number variation within the genome of the test cells. Data are typically normalized so that the modal ratio for the genome is set to some standard value, typically 1.0 on a linear scale or 0.0 on a logarithmic scale. Additional measurements such as fluorescence in situ hybridization (FISH) or flow cytometry (Mohapatra G. et al., 1997 Genes Chromosomes Cancer, 20: 311-19) can be used to determine the actual copy number associated with a ratio level.

Array CGH has been implemented using a wide variety of techniques. The initial approaches used arrays produced from large-insert genomic clones such as bacterial artificial chromosomes (BACs). Producing sufficient BAC DNA of adequate purity to make arrays is arduous, so several techniques to amplify small amounts of starting material have been employed. These techniques include ligation-mediated polymerase chain reaction (PCR) (Snijders A. et al., 2001 Nat. Genet. 29:263-64), degenerate primer PCR using one or several sets of primers, and rolling circle amplification. BAC arrays that provide complete genome tiling paths are also available. Arrays made from less complex nucleic acids such as cDNAs, selected PCR products, and oligonucleotides can also be used. Although most CGH procedures employ hybridization with total genomic DNA, it is possible to use reduced complexity representations of the genome produced by PCR techniques. Computational analysis of the genome sequence can be used to design array elements complementary to the sequences contained in the representation. Various single nucleotide polymorphism (SNP) genotyping platforms, some of which use reduced complexity genomic representations, are useful for their ability to determine both DNA copy number and allelic content across the genome.

The different basic approaches to array CGH provide different levels of performance, so some are more suitable for particular applications than others. The factors that determine performance include the magnitudes of the copy number changes, their genomic extents, the state and composition of the specimen, how much material is available for analysis, and how the results of the analysis will be used. Many applications use reliable detection of copy number changes of much less than 50%, a more stringent requirement than for other microarray technologies. Note that technical details can play a role in assay performance and different implementations of methods using the same array CGH approach can yield different levels of performance. Various CGH methods are known in the art and are equally applicable to one or more methods of the present invention. For example, CGH methods are disclosed in U.S. Pat. Nos. 7,034,144; 7,030,231; 7,011,949; 7,014,997; 6,977,148; 6,951,761; and 6,916,621, the disclosure from each of which is incorporated by reference herein in its entirety.

The data provided by array CGH are quantitative measures of DNA sequence dosage. Array CGH provides high-resolution estimates of copy number aberrations, and can be performed efficiently on many samples. The advent of array CGH technology makes it possible to monitor DNA copy number changes on a genomic scale and many projects have been launched for studying the genome in specific diseases. For example, chromosomal aberrations play a pivotal role in cancer progression, where knowledge of genomic instability promises to lead to improved cancer diagnostics and treatments.

The mechanism of cancer progression involves chromosomal aberrations, including amplification of oncogenes and deletion of tumor suppressor genes. These chromosomal aberrations can be revealed via array CGH analysis. As the effective resolution of array CGH techniques increases, an increasing rate of discovery of medically relevant dosage aberrations will result. However, interpreting the primary data becomes more complex due to the need to better understand normal polymorphisms, both in the germline and tumor genome. The further elucidation of dosage polymorphisms remained experimental rather than a computational endeavor without high quality aCGH data available on a very large number of normal individuals. Understanding those dosage polymorphisms that are detectable by array CGH can be used so that normal variations are not falsely associated with disease, and conversely to determine if some so-called normal variations can underlie certain disease susceptibilities.

Specifically, one embodiment of the array CGH procedure includes the following steps. First, large-insert clones such as BACs are obtained from a supplier of clone libraries. Then, small amounts of clone DNA are amplified by either degenerate oligonucleotide-primed (DOP) PCR or ligation-mediated PCR in order to obtain sufficient quantities needed for spotting. Next, these PCR products are spotted onto glass slides using microarray robots equipped with high-precision printing pins. Depending on the number of clones to be spotted and the space available on the microarray slide, clones can either be spotted once per array or in replicate. Repeated spotting of the same clone on an array increases precision of the measurements if the spot intensities are averaged, and allows for a detailed statistical analysis of the quality of the experiments. Subject and control DNAs can be labeled with either Cy3 or Cy5-dUTP using random priming and are subsequently hybridized onto the microarray in a solution containing an excess of Cot1-DNA to block repetitive sequences. Hybridizations can be performed manually under a coverslip, in a gasket with gentle rocking, or automatically using commercially available hybridization stations. These automated hybridization stations allow for an active hybridization process, thereby improving the reproducibility as well as reducing the actual hybridization time, which increases throughput. The hybridized DNAs can be detected through the two different fluorochromes using standard microarray scanning equipment with a scanning confocal laser or a charge coupled device (CCD) camera-based reader, followed by spot identification using commercially or freely available software packages. Any conventional fluorochrome can be utilized in the invention. These are well known and commercially available. Specific examples of detectable molecules include radioactive isotopes such as P32 or H3, fluorophores such as fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as alkaline phosphatase, horseradish peroxidase, I 2-galactosidase, and hapten conjugates such as digoxigenin or dinitrophenyl, etc. Other detectable markers include chemiluminescent and chromogenic molecules, optical or electron density markers, etc. The probes can also be labeled with semiconductor nanocrystals such as quantum dots (i.e., Qdots), described in U.S. Pat. No. 6,207,392. Qdots are commercially available from Quantum Dot Corporation. Additional examples of reagents which are useful for detection include, but are not limited to, radiolabeled probes, fluorophore-labeled probes, quantum dot-labeled probes, chromophore-labeled probes, enzyme-labeled probes, affinity ligand-labeled probes, electromagnetic spin labeled probes, heavy atom labeled probes, probes labeled with nanoparticle light scattering labels or other nanoparticles or spherical shells, and probes labeled with any other signal generating label known to those of skill in the art. Non-limiting examples of label moieties useful for detection in the invention include, without limitation, suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland; a luminescent material such as luminol; light scattering or plasmon resonant materials such as gold or silver particles or quantum dots; or radioactive material include 14 C, 123 I, 124 I, 125 I, 131 I, Tc99m, 35 S or 3 H.

Examples of labels include, but are not limited to, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, and electrochemical detection moieties. Genotyping using a microarray can be performed using any of a variety of methods, means and variations thereof for carrying out array-genotyping analysis.

Furthermore, backbone labels are nucleic acid stains that bind nucleic acid molecules in a sequence independent manner. Examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

The increase in data obtained through high-density arrays uses standardized storage systems as well as thorough statistical tools, similar to those used for microarray-based gene expression profiling. Owing to the complicated process of producing and hybridizing spotted microarrays, a certain degree of systematic variation does exist in the data produced. Normalization of microarray data can be used to eliminate such systematic variation and, therefore, can be a preprocessing step in the analysis of almost all microarray data. After data normalization, automated statistical procedures are used for reliable detection of genomic copy number changes. Finally, digitized intensity differences in the hybridization patterns of the DNAs onto the cloned fragments can be interpreted as copy number differences between the test and reference genomes. This technique, once established and validated, allows high-throughput DNA copy number screening with a resolution limited only by the size of the clone fragments or oligonucleotide length/spacing used (typically ~100 kb using BAC arrays but essentially down to ~10 bp using oligonucleotide arrays, see Table 4).

The information included in the normal copy number variation KMT (or as a component of the NVE) is obtained by screening the genome of a large population of individuals using conventional techniques of array CGH. The samples from these individuals for evaluation of the nucleic acid can include any conventional biological sample for obtaining the necessary genomic material. The samples can be cells, blood, bodily fluids, amniotic fluid, biopsies, or tissue. The bodily fluid can be, e.g., aqueous humour, vitreous humour bile, blood serum, blood plasma, whole blood, breast milk, cerebrospinal fluid, chyle, chyme, interstitial fluid, perspiration, phlegm, cerumen, endolymph, perilymph, female ejaculate, gastric juice, mucus, peritoneal fluid, pleural fluid, pus, synovial fluid, transcellular fluid, vaginal secretion, saliva, sebum, sweat, tears, amniotic fluid, vomit, or urine. The tissue can be, e.g., connective tissue, muscle tissue, nervous tissue or epithelial tissue. A sample can be from an organ, e.g., skin, heart, lung, eye, brain, liver, spleen, spinal cord, peripheral nerves, blood vessels, blood, skeletal muscles, smooth muscles, bones, cartilage, tendons, ligaments, nose, trachea, mouth, esophagus, small intestine, large intestine, kidney, ureters, bladder, urethra, hypothalamus, pituitary, thyroid, pancreas, adrenal gland, ovaries, oviducts, uterus, mammary glands, testes, seminal vesicles, lymph, lymph nodes, lymph vessels, and white blood cells. The sample can comprise DNA, RNA, mRNA, siRNA, shRNA, miRNA, cDNA, cell-free DNA, or cell-free RNA. Furthermore, samples can be fresh, from cells/tissue in culture or from archival cells/tissue, such as frozen samples, Guthrie cards, cord blood, or placenta. The sample can be flash frozen, e.g., in liquid nitrogen. The sample can be a formalin fixed paraffin-embedded tissue sample. Sampling in this context includes conventional methods in the art of obtaining a blood sample or cell sample, including buccal, nasal or throat swabs, or collection of saliva. The sample can be collected by the subject or by a healthcare provider, e.g., a physician, nurse, dentist, or surgeon.

In addition, in one or more methods of the invention, the samples for genomic evaluation can be obtained from a newborn, child, pre-teen, teen, adult, or elderly subject. In another embodiment, a sample is obtained via amniocentesis or chorionic villus sampling to provide a DNA sample for genomic analysis. The sample can be obtained, e.g., by a biopsy, e.g, open biopsy (i.e. a surgical incision is made through the skin), closed biopsy, or fine needle aspiration. In some embodiments, DNA samples are prepared from original tissue sources and not from cell lines created from said tissue sources, which frequently contain chromosomal changes due to the cell culturing process itself, that is, the chromosomal changes are not present in the individual's germline.

Tuning the NVE for Optimal Discovery Power

Normal variation underlies the NVE's ability to reveal causative genetic variants of disease. When the NVE, which includes a KMT containing information on the frequencies of CNVs in a normal cohort or population, is employed in the CNV Beacon method, rare variant CNVs (beacons) can lead to discovery of disease genes and thus enable rapid, cost-effective identification of the additional disease-causing mutations of any size or type. Table 5 models these concepts to tune the size of the KMT (i.e., in Table 5, the number of "Normals Tested") used in the NVE for discovery of common, complex disease biomarkers, which in one embodiment enables identification of rare variants that are causative of disease.

a good disease biomarker candidate. In one embodiment a larger KMT/NVE can be constructed to find causative variants for lower prevalence diseases.

A KMT/NVE with well-phenotyped apparently healthy subjects (i.e., normal individuals) can be built but there is still a chance that affected individuals for the disease being studied can be present in the KMT/NVE. Also, for common, complex diseases, it is not uncommon to observe lower penetrance for a given genetic variant so apparently healthy individuals with a disease-causing variant can be present in the KMT/NVE. This scenario is modeled for diseases with 1% and 5% prevalence rates and it was found that the KMT/NVE is still well-powered to find disease-causing CNVs despite a KMT/NVE containing both normal CNVs and CNVs for an occasional affected individual(s) for the disease being studied. For example, for a disease that occurs in 1 in 100 (1% prevalence) and the number of affecteds tested that have the variant is 100 in 1,000, it is expected to find only 1 individual in the normals with this disease-associated variant when using an unselected cohort for the normals. If 1,000 "nor-

TABLE 5

Simulated Odds Ratio (OR) Analysis for Rare CNV Discovery with the NVE

| Affected with Variant (p)[b] | Affected Tested | Normals with Variant (q)[c] | Normals Tested | Affected Odds [p/(1,000 − p)] | Normals Odds [q/(NVE size − q)] | OR[d] |
|---|---|---|---|---|---|---|
| 0.1-3% rare variant occurrence in Affected cohort | | | | | | |
| 0% rare variant occurrence in Normal cohort (from apparently healthy population) | | | | | | |
| 1 | 1,000 | 1 | 1,000 | 0.0010 | 0.0010 | 1.0 |
|  |  |  | 3,000 | 0.0010 | 0.0003 | 3.0 |
|  |  |  | 5,000 | 0.0010 | 0.0002 | 5.0 |
| 3 | 1,000 | 1 | 1,000 | 0.0030 | 0.0010 | 3.0 |
|  |  |  | 3,000 | 0.0030 | 0.0003 | 9.0 |
|  |  |  | 5,000 | 0.0030 | 0.0002 | 15.0 |
| 10 | 1,000 | 1 | 1,000 | 0.0101 | 0.0010 | 10.1 |
|  |  |  | 3,000 | 0.0101 | 0.0003 | 30.3 |
|  |  |  | 5,000 | 0.0101 | 0.0002 | 50.5 |
| 30 | 1,000 | 1 | 1,000 | 0.0309 | 0.0010 | 30.9 |
|  |  |  | 3,000 | 0.0309 | 0.0003 | 92.8 |
|  |  |  | 5,000 | 0.0309 | 0.0002 | 154.6 |
| 1% (1 in 100) disease prevalence (e.g., autism and schizophrenia) | | | | | | |
| Normals from unselected population will contain 10 with disease[e] | | | | | | |
| 3 | 1,000 | <1 | 1,000 | 0.0030 | 0.0010 | 3.0 |
| 10 |  | <1 |  | 0.0101 | 0.0010 | 10.1 |
| 30 |  | <1 |  | 0.0309 | 0.0010 | 30.9 |
| 100 |  | 1 |  | 0.1111 | 0.0010 | 111.0 |
| 300 |  | 3 |  | 0.4286 | 0.0030 | 142.4 |
| 5% (1 in 20) disease prevalence (e.g., T2D and hypertension) | | | | | | |
| Normals from unselected population will contain 50 with disease[e] | | | | | | |
| 3 | 1,000 | <1 | 1,000 | 0.0030 | 0.0010 | 3.0 |
| 10 |  | 1 |  | 0.0101 | 0.0010 | 10.1 |
| 30 |  | 2 |  | 0.0309 | 0.0020 | 15.4 |
| 100 |  | 5 |  | 0.1111 | 0.0050 | 22.1 |
| 300 |  | 15 |  | 0.4286 | 0.0152 | 28.1 |

[a]Assume Normal Variation Engine (NVE) size of 1, 3, or 5 thousand apparently healthy individuals.
[b]Represents the assumed number of Affected with a particular rare variant (typical frequency 0.1-3%).
[c]Assume the Normal cohort has no or only 1 occurrence of a particular rare variant.
[d]Odds Ratio (OR) = Affected Odds/Normal Odds; assume a value of 1 occurrence in the Normals if 0 are detected.
[e]Calculated from the assumed common disease incidence (1% or 5%) in the population at large for a fixed NVE size of 1,000 invidivuals. This also models variants of lower penetrance.

Examples of OR calculations are presented in Table 5 for varying prevalence rates of disease and different size KMTs/NVEs (Normals Tested). For example, if 10 affected patients have a particular CNV out of 1,000 tested, and only 1 (or 0, since 1 is typically assumed to calculate the OR in instances of zero events found) is found in a KMT/NVE comprising 1,000 normals, then the OR=10.1, thus indicating the CNV is mals" are tested for the affected variant, 100 will have the disease but only 1 is likely to have the variant since its prevalence in the affected cohort is in 1 in 100 (i.e, 100 in 1,000 as reported in Table 5). From the range of ORs obtained for both the 1% and 5% disease prevalence rates using an unselected (i.e. potentially tainted) cohort of normals, it is apparent that the NVE driven rare variant discovery approach is still highly effective in discerning disease-causing variants from benign ones. Finally, it is noted that while rare CNVs are the type of molecular biomarkers used to power the NVE, these methods can be utilized using other types of molecular biomarkers including, but not limited to, disease vs. normal differences in epigenetic marks, alternative splicing, microRNA levels, protein levels, etc.

Using the CNV Beacon Method to Discover Disease Genes and Causative Biomarkers/Mutations The examples annotated/highlighted in Tables 2 and 3 (vide supra) are representative of the numerous diseases, whether single gene (Mendelian) disorders or complex diseases involving several genes/loci, for which CNVs are the causative biomarker/mutation in a subset of patients with a given disease. In other words, these disease-causing CNVs are "beacons" of disease genes. It is anticipated that for virtually every gene/locus associated with or causal of disease or drug response (efficacy or serious adverse events), CNVs will be found within the gene/locus in a subset of the individuals in the affected cohort (e.g., those with the disease phenotype or experiencing an adverse reaction to drug). Subsequent sequencing of these genes/loci using genomic DNA from said affected cohort will uncover additional genetic variants (i.e., those below the resolution of the array CGH platform used to generate the KMT/NVE or that are copy number neutral and thus undetectable by array CGH) that are causal or associated with the disease or drug response. For example, by CNV analysis of an affected cohort and interpretation with the KMT/NVE to discern benign vs. pathogenic CNVs, perhaps ~10% of affected patients can be found to have a causative CNV within a given gene and subsequent sequencing of said gene in the affected and normal cohorts can reveal the presence of other pathogenic variants (typically one variant in each patient) in another 10-50% of patients. Thus, overall (collectively considering the contribution of pathogenic CNVs, indels, SNVs, etc.), the set of causative genetic variants that explain the disease in 20-60% of affected patients can be found (see FIG. 2). Thus, through detection of CNVs in an affected cohort and their interpretation using an appropriately sized KMT/NVE containing CNV frequency data on normal individuals, the genetics of most single gene and complex disorders can be rapidly and cost-effectively solved.

In one embodiment, a genetic variant is identified by the CNV Beacon method in a subject of a particular cohort. In one embodiment the CNV Beacon method is directed to identification of one or more subpopulations from said cohort in which a therapeutic drug is useful in treatment, where the therapeutic drug is identified as useful if the benefits outweigh any adverse effects or the therapeutic drug is identified as not useful if the adverse effects outweigh any benefits. In one embodiment the subject is responsive to a therapeutic drug. In another embodiment the subject is resistant to or unaffected by the therapeutic drug. In a preferred embodiment, the KMTs incorporating data sets of genetic variants identified by the CNV Beacon method for a cohort or a subgroup(s) within a cohort are compared to genetic variants identified by the CNV Beacon method in a subject to provide frequencies of the genetic variants identified by the CNV Beacon method in order to allow a determination for whether one or more genetic variants in subgroup(s) of said cohort are identified for whom said drug should be prescribed (i.e., is useful in therapy) or should not be prescribed (i.e., drug adverse effects outweigh any benefits) in said subject. Also, these KMTs can be utilized to follow therapeutic drugs in use after regulatory approval, such as by the FDA, to continue monitoring the drug and its efficacy or adverse reaction within identified subpopulations of the group.

In one embodiment this analysis provides a snapshot of normal and abnormal genetic variants coupled with a linkage to therapeutic drugs and treatments targeted to a subject's genetic profile. In particular, one embodiment permits the identification of subjects who can be treated effectively with a therapeutic drug or those who might have an adverse side-effect from a therapeutic drug. This subject stratification based on genetic variants identified by the CNV Beacon method is particularly useful to focus treatment into the short window of time that may produce results and reduce any detours or damaging treatments for a subject with a disease or condition that is a candidate for treatment with the therapeutic drug. This stratification can also facilitate the segregation of a cohort of subjects responding to therapeutic drugs in a clinical trial from those not responding or experiencing adverse reactions so that the therapeutic drugs may be rescued and targeted to subpopulations for whom the therapeutic is efficacious.

In another embodiment genetic variants identified by the CNV Beacon method can be used in predictive or personalized medicine. Healthcare systems recognize that the personalized medicine approach has the greatest potential for treating each patient uniquely, specifically and optimally. The use of the KMTs can be quite important for interpreting chromosomal and genetic variant changes relative to certain disease states. Genes involved in pathological chromosomal and/or genetic variant changes represent targets for therapeutic treatment and the linkage of the genetic makeup to an isolated population of patients allows personalized treatment. Personalized medicine can benefit from greater cooperation between diagnostic and therapeutic organizations in the development of new technologies and products but also in review of existing medications. The use of pharmacogenomics and toxicogenomics to compare the patient's sample against the KMTs for genetic variants identified by the CNV Beacon method allows the identification of the most effective drugs for certain patient populations. Included in this evaluation is the genetic basis of the metabolism of drugs, including toxicity, to assist targeted therapies.

Personalized medicine is especially relevant in the field of pharmacogenomics. Pharmacogenomics information is especially useful in clinical settings where correlation information is used to prevent drug toxicities. For example, patients are often screened for genetic variants in a gene or chromosomal region, which correlate to a phenotype of medical importance (e.g., disease state). However, only a small percentage of observed drug toxicities have been explained adequately by the set of pharmacogenomic markers available to date. In addition, "outlier" individuals, or individuals experiencing unanticipated effects in clinical trials (when administered drugs that have previously been demonstrated to be both safe and efficacious), cause substantial delays in obtaining FDA drug approval and may even cause certain drugs to come off market, though such drugs may be efficacious for a majority of recipients.

Genomic differences have long been recognized as influencing how patients respond to drugs. However, pharmaceutical companies generally have not considered genomic differences between patients in developing and implementing clinical trials or in the marketing of approved drugs. By correlating genomic variation with drug response in clinical trials, it is possible to improve the drug development and marketing process. For example, pharmaceutical companies could use the correlation data from earlier stages of clinical trials to make more informed decisions on whether or not to continue trials, enter later phases of trials or which patients to enroll in later stages (e.g., phase III or IV). For example, enrolling patients with genetic predisposition for positive drug response can improve the therapeutic index for these patients and improve the possibility of regulatory approval.

Furthermore, understanding the correlation between genomic differences and drug response can enable pharmaceutical companies to improve drug marketing by identifying segments of the population for whom particular drugs are likely to be more effective than other drugs, and encouraging physicians to preferentially prescribe such drugs to these patients. The business methods include licensing the KMTs to pharmaceutical companies for use during their research and clinical trials to interpret and optimize results as much as possible. Alternatively, there are methods of forming relationships or partnerships with the pharmaceutical companies to engage in research of the genomic features of the patient population in conjunction with developing clinical trials. As a part of the agreement, the business would provide the powerful KMTs and the company would provide additional information gleaned about the genome during the trials and analysis. Marketing to physicians can be accomplished by continuing medical education, peer-review journals, Internet, social media, print advertising or direct sales calls. In addition, by using the information disclosed herein a company can better market a drug by segregating a responder population from a non-responder population, or by segregating a population that encounters negative side effects (or even toxicity) from a population that does not suffer negative effects. This may further allow a company to keep a drug on the market that would otherwise be withdrawn or to reintroduce a drug that has already been withdrawn due to adverse effects.

Drugs are typically developed to interact with a single version of a gene product, e.g., protein or receptor in human and non-human animal subjects. A drug may therefore, for example, only be effective in individuals that have a particular variation encoding the specific protein or receptor for which the drug was designed. Individuals, who do not have a genetically caused variation (e.g., a causative mutation) in these regions or in regions involved in the metabolism of the drug, may not respond to the drug or may experience adverse side effects, such as increased toxicity for example.

The methods used by the pharmaceutical industry to develop new drugs and to improve existing drugs can be changed when genetic variations are taken into account. Genetic variations can play a significant role in all stages of research and development and drug discovery. Genetic variation information can also be used to improve drugs already on the market by providing information to better select drugs for a particular patient.

In another embodiment, drugs can interact, directly and/or indirectly, with a variety of different proteins that are encoded and regulated by different genomic regions. Therefore, more than one genomic region can determine how an individual responds to a given drug. The inventions herein can be used to identify such multiple regions. As genetic variations are better understood, it is clear that an individual's response to a given drug is dependent upon that individual's unique genome or more specifically variations within the genome. The information generated can also be used to create diagnostic kits to identify the genomic markers that are linked to conditions, diseases or results with a drug. These tests can be used to diagnose and to predict the best course of treatment.

In another embodiment, the information on genetic variants identified by the CNV Beacon method and the KMT can be used in providing diagnostic assays for medically relevant biomarkers and assisting in the development and research efforts for additional markers. Another embodiment provides "translational medicine" to accelerate research discoveries to patients as quickly as possible. This includes a CLIA lab performing diagnostic evaluations of the genetic variants identified by the CNV Beacon method utilizing both microarray based or non-microarray based analyses (e.g., sequencing or PCR).

In one embodiment the CNV Beacon method comprises steps performed for causative gene/mutation discovery and validation that: 1) perform high resolution whole-genome array CGH on the affected cohort, 2) interpret the statistical significance of the CNVs found in the affected cohort relative to the CNVs in a normal cohort previously annotated in the KMT/NVE, and 3) sequence the candidate causal genes/loci (i.e., targeted sequencing) identified in step 2 in both the affected and normal cohort to reveal additional genetic variants causative of disease. In some embodiments, a sufficiently sized and multiethnic normal cohort is used to generate the CNV data used in the KMT so that it needs to be created only one time for use in solving most diseases in most populations, or, in another embodiment, the KMT is created using a particular ethnic group or gender to enhance the efficiency and discovery power for disease or conditions specific to these particular cohorts. In another embodiment, a biorepository of the normal individual (apparently healthy) DNA samples used for generating the KMT's normal CNV data is maintained for efficient and continual access for targeted sequencing (step 3 of the CNV Beacon method, vide supra), validation studies, and diagnostic test development, which uses testing of a large number of controls to establish the sensitivity and specificity of the test. In another embodiment, the biorepository of normal DNA samples is linked to electronic medical records that can allow for further refinement of the data content within the KMT/NVE and/or more detailed mapping of genotypes to phenotypes, which can enable more precise subtyping of a patient's disease, thus facilitating personalized medicine and prescription of targeted therapies.

In another embodiment, the KMT contains the full genome sequence or a subset of data from the full genome sequence for individuals comprising said KMT. It can be appreciated by those skilled in the art that sequencing technologies will soon be sufficiently advanced to enable rapid and low-cost sequencing of an individual's whole genome. Once completed, the full spectrum of genetic variants present in an individual's genome will be known (for example, as compared to the first human genome sequenced and commonly termed the Reference Sequence), but what will not be known is the frequency of each variant within the population at large and, thus, the functional significance of any one variant in normal and disease biology will not be known. As for CNVs, interpretation of any size or type of genetic variant as pathogenic or benign in an individual, can involve a comparison to a very large number of individuals (due to the previously under-appreciated extent of genetic variation in humans, see Pang A. et al. Genome Biol. 2010; 11(5):R52. Epub 2010 May 19) that are unaffected by the disease or condition. In this regard, consideration of all genetic variants (i.e., the full genome sequence of individuals in an affected and unaffected cohort) substantially increases the genetic variation "search space" and thus the complexity of discerning pathogenic vs. benign variants. Such full genome analysis can use tens of thousands, 100,000, or even as many as 1,000,000 individuals to fully ascertain the spectrum of genetic variation in the population for accurate interpretation of pathogenic vs. benign variants. In this case, one embodiment of the CNV Beacon method is to informatically filter the full genome sequence so that only the CNVs and other larger sized structural variants (e.g., translocations and inversions, but can also include in silico assessment of functionally relevant indels, nonsynonymous SNVs, etc.) are considered in the initial analysis of an affected cohort. Once a disease gene or locus is revealed in the affected cohort relative to the normal cohort (KMT) by analysis of the CNVs/structural variants, the sequence data for these disease candidate regions can be informatically assessed in both cohorts to further validate the candidate disease gene as causal and also to reveal the full spectrum of disease-causing variants. Thus, in one embodiment, only in silico experiments/analyses need to be performed if the affected and unaffected cohorts are of sufficient size to establish statistical significance for any given variant within a population. In another embodiment, the full genome sequence is determined for normal individuals comprising the KMT (e.g., 1,000 to 10,000 individuals) and the affected cohort's CNVs are determined by array CGH and/or sequencing of the affecteds full genome or a subset of loci (e.g., the candidate disease genes identified via CNV analysis alone) for interpretation of candidate causal genes/loci of a disease or condition. For rapid and low-cost validation of benign vs. pathogenic variants, another embodiment would involve sequencing the full genome of a smaller number of unaffected vs. affected individuals, filtering the data for CNVs in said unaffected and affected cohorts, targeted in silico analysis of all genetic variants within a CNV Beacon identified gene/loci, and validation/replication of all candidate causal variants (CNVs, indels, SNVs, etc.) via low-cost genotyping in larger unaffected and affected cohorts.

It is now known that human genomes are rife with normal CNVs, a finding that was hinted at in papers appearing in 2004 and was the basis of the utility of a normal variation KMT (U.S. Pat. Nos. 7,702,468 and 7,957,913) in discovery and validation of disease genes/loci in genomes. The first systematic genome-wide assessment of CNVs in human genomes was not completed until 2006 (Redon R. et al. 23 Nov. 2006 *Nature* 444:428-429) and then only on 270 HapMap samples (collected for the HapMap projects but are not carefully screened for health status so the cohort cannot be classified as "apparently healthy,"). Further, even higher resolution CNV maps involved only 40 HapMap samples (Conrad D. et al. Nature. 2010 Apr. 1; 464:704-12) for discovery so CNVs remain under ascertained in public databases for the purpose of discovery of disease and drug response genes. Rare CNVs, which are anticipated to encompass a large number of disease causing variants (Bodmer W. and Bonilla C. Nat Genet. 2008 June; 40:695-701), can be greatly under-ascertained in the population, thus precluding identification of causative genes/mutations for single gene and complex diseases—an unsolved problem for a majority of diseases. The contribution of rare variants in general (i.e, not only CNVs but also SNVs, indels, etc.) to common, complex diseases was only recently understood by those skilled in the art (Goldstein D. N. Engl. J. Med. 2009 Apr. 23; 360:1696-8; Manolio T. et al. Nature. 2009 Oct. 8; 461:747-53) to be significant as previous consensus held that common variants caused common disease (i.e., the Common Disease—Common Variant hypothesis). Thus, the wide-ranging impact of CNVs, particularly rare CNVs and other rare variants found via use of the CNV Beacon method, on normal biology and disease was under-appreciated by those skilled in the art and not understood that methods for evaluating genetic disorders by interpreting genomes with a KMT (such as described in U.S. Pat. Nos. 7,702,468 and 7,957,913) and the present invention, the CNV Beacon method, can be enabled with statistically rigorous interpretation of which CNVs are pathogenic vs. benign. For example, with regard to statistical rigor and execution of KMT/NVE and CNV Beacon methods, while normal CNVs have been annotated in the publicly available Database of Genomic Variants (DGV), which functions as a resource of normal CNV information for the genetics research community, there are three caveats to note for this publicly annotated CNV data: 1) the data are generated on a wide variety of CNV detection platforms (FISH, BAC CGH arrays, oligo CGH arrays, SNP arrays, and sequencing) of broadly varying resolution, 2) the samples used are not all carefully phenotyped and come from numerous labs around the world so the data are tainted with disease-causing CNVs, 3) a large number of the CNVs have not been validated, and 4) the samples used to populate the database are not readily available for validation and other follow-up studies and diagnostic test product development. Thus, the embodiments of the KMT/NVE noted vide supra, and usefulness of the present invention, are dependent on the size of the normal cohort, the source of the normal cohort, IRB-approved informed consent of the normal cohort, ongoing access to the DNA samples (i.e., the biorepository) used to create the KMT/NVE, and collection of CNV data at sufficiently high resolution on a single CNV detection platform to overcome the sampling noise of the measurements for reliable determination of CNVs on a genome-wide basis and at gene-level resolution.

Validating Candidate Disease Genes and Causative Biomarkers/Mutations

As outlined supra, performing a Tier 1 study with the NVE can be only the first step in finding causative disease (or drug response) biomarkers. While it is a powerful means to distill out a set of biomarker candidates with metrics of causality (high ORs), additional work can be involved to qualify each candidate as causative of a disease with the level of confidence specified to include it in a diagnostic test. In one embodiment it is a high level of confidence. Replication with fresh disease cohorts further verify if candidate CNVs are causative of the disease under investigation. However, other types of validation work are also commonly performed to validate biomarker candidates.

One type of validation is to perform PCR assays within a CNV to confirm a copy number change (e.g., assuming 2 copies is the normal state, then 1 copy indicates a deletion and 3 copies indications a duplication event). For CNVs, deletions and duplications can be evaluated further by sequencing across the pair of DNA breakpoints and delineating the size and location of the CNVs. This can be done using a particular type of PCR assay termed junction fragment PCR, which generates a PCR product spanning the breakpoint; however, the method uses CNV detection at high enough resolution to localize the breakpoint interval to a size <10 Kb in order for a PCR to generate a PCR product. If the whole genome arrays CGH results are not of sufficient resolution to perform junction fragment PCRs, deletion and duplication breakpoints can be fine-mapped using a higher resolution custom oligonucleotide CGH array containing oligonucleotide probes spaced ~10 bp apart (i.e., overlapping). Such significantly higher resolution oligo CGH experiments often refine breakpoint intervals to <500 bp, which then easily enable design and performance of junction fragment PCR assays (Roohi J. et al. 2009 *J. Med. Genet.* 46:176-182). In one embodiment an advantage of junction fragment PCR is that the PCR products can be sequenced to reveal the actual DNA sequence at the breakpoints, which can be useful in determining the mechanism of CNV formation (e.g., via Alu sequences, which are a type of repeat sequence element in the genome and are a common mechanism of deleterious recombination events recombination) or for the design of additional validation assays and in diagnostic test development. FISH validation is another commonly used cytogenetic validation and mapping method to verify the CNVs.

Several types of validation can be performed on candidate causal CNVs after their initial identification using the KMT/NVE. Examples include, but are not limited to:
1. In silico investigation of the candidate gene to assess if the known biology implicates it in the disease under investigation and to assess if mutations (of any type) have been reported by others that link it to the disease.
2. In silico investigation of the candidate gene mutations (e.g., the deletions and/or duplications) to predict if they are deleterious to gene function.
3. FISH to validate and grossly map the CNVs.
4. Ultra-high resolution custom array CGH to validate the CNVs and fine-map their breakpoints.
5. Junction fragment PCR assays to validate the CNVs and produce PCR products for sequencing.
6. Sequencing the junction fragment PCR products to validate the breakpoints and identify the adjacent sequences.
7. Sequencing the candidate gene to find other potentially causative mutations, which themselves can be assessed in silico to determine if the candidate gene mutations are predicted to be deleterious to gene function.

In one embodiment, array CGH is performed to find candidate causal CNVs and these are then sequenced to identify the full spectrum of mutations within the gene/locus that can be causal of the disease or condition under investigation. The sequencing can be performed using any sequencing method described herein.

Building a Commercial-Scale NVE

In some embodiments, a high resolution commercial-scale NVE enables at least 10× greater discovery power and several orders of magnitude greater output of disease-causing rare variants. Newer oligonucleotide CGH platforms can pinpoint single genes in the Tier 1 discovery data since their mapping resolution is ~1,000-3,000 bp (i.e., <10,000 bp, the average size of a gene). There are several attributes of a commercial-scale NVE that contribute to its gene/variant discovery power. These are:
1. Use of a significantly higher resolution oligo array CGH platform yields at least 10× more CNVs per individual than what is currently in use today, greatly enriching both the NVE normal CNV content and the list of candidate disease-causing CNVs for the disease cohorts under investigation.
2. Use of a cohort size of at least 1,000 normal individuals, with expandability to 10,000, to further enrich the NVE normal CNV content, which increases the statistical significance (i.e., medical relevance) of causative disease mutations assessed with the NVE.
3. Use of a well-phenotyped normal cohort with fully consented access to electronic medical records and ongoing access to the DNA samples for discovery, validation, and product development efforts enables accurately mapping genotypes to phenotypes for the causative biomarkers that can be used in diagnostic tests or for therapeutics development.

NVE Technology is Broadly Applicable

Examples of rare CNV findings found by others in multiple diseases (see Table 6) underscore two key points, 1) rare CNVs are generally causative of common diseases, and 2) the KMT/NVE technology is broadly applicable in finding disease genes as evidenced by others essentially using the NVE methodology. Nearly all of the findings in Table 6 were the result of reanalysis of SNP array genome-wide association study (GWAS) data that failed to yield the expected common variants with ORs >~1.5 (as noted supra, rare variants, not common variants, are now thought by those skilled in the art to be a major cause of common diseases in addition to rare diseases). Even with these lower powered SNP arrays, which have poor probe coverage of the "dark matter" of the genome (dynamic regions in the genome often more prone to recombination due to more repetitive sequences and believed by many to contain the "missing" disease-causing variants), CNVs of much greater significance (ORs 5-68) were found in the disease cohorts. These rare variants, found with lower power array platforms (as evidenced by their relatively large size, 0.2-1.6 Mb), represent only a very small fraction of what will eventually be found as, to date, less than 5% of the genetic component of disease has been identified for nearly all common diseases. Also, the fraction of affected represented by these rare CNVs within each disease cohort (patients with the CNV/total patients in the disease cohort) range from 0.2-1%, which is exactly the range modeled in Table 5 and the KMT/NVE and CNV Beacon method are well-powered to find.

TABLE 6

Survey of rare variant CNVs reported for common, complex diseases

| Disease | Genome Location (Mb)[a] | Cytoband | Size (Mb) | Variant Type | Affected with CNV | Affected TOTAL | Normals with CNV | Normals TOTAL | OR[c] | Source[d] |
|---|---|---|---|---|---|---|---|---|---|---|
| Autism | chr16: 29.56-30.11 | 16p11.2[b] | 0.55 | del | 4 | 712 | 0 | 837 | 4.7 | 1 |
|  | chr16: 29.50-30.11 | 16p11.2[b] | 0.60 | del/dup | 24 | 2,252 | 12 | 23,502 | 21.1 | 2 |
| Schizophrenia | chr1: 142.54-145.02 | 1q21.1 | 0.86-2.81 | del | 10 | 3,391 | 1 | 3,181 | 9.4 | 3 |
|  | chr15: 28.68-30.65 | 15q13.3 | 0.53-2.47 | del | 9 | 3,391 | 0 | 3,181 | 8.5 | 3 |
|  | chr22: 17.11-19.92 | 22q11.2 | 0.78-2.68 | del | 13 | 3,391 | 0 | 3,181 | 30.0 | 3 |
|  | chr1: 144.94-146.29 | 1q21.1 | 1.35 | del | 11 | 4,718 | 8 | 41,199 | 12.0 | 4 |
|  | chr15: 28.72-30.30 | 15q13.3 | 1.58 | del | 7 | 4,213 | 8 | 39,800 | 8.3 | 4 |
|  | chr16: 29.56-30.11 | 16p11.2[b] | 0.55 | dup | 21 | 4,551 | 2 | 6,391 | 14.8 | 5 |
| Epilepsy | chr15: 28.75-30.20 | 15q13.3 | 1.45 | del | 19 | 1,762 | 8 | 50,115 | 68.3 | 6, 7 |
| Obesity | chr16: 28.73-28.95 | 16p11.2 | 0.22 | del | 21 | 5,231 | 3 | 14,800 | 19.9 | 8, 9 |

[a]Approximate chromosome (chr) locations are reported and each contains multiple genes.
[b]Deletions (del) more prevalent in Autism and duplications (dup) more prevalent in schizophrenia.
[c]For Odds Ratio (OR) calculations with zero CNVs in the Normals (controls), a value of 1 is used. For Epilepsy and Obesity, combined studies are reported.
[d]Sources: 1) Kumar R et al. Hum Mol Genet. 2008 Feb 15; 17(4): 628-38. Epub 2007 Dec 21. 2) Weiss L et al. N Engl J Med. 2008 Feb 14; 358(7): 667-75. Epub 2008 Jan 9. 3) International Schizophrenia Consortium Nature. 2008 Sep 11; 455(7210): 237-41. Epub 2008 Jul 30. 4) Stefansson H et al. Nature. 2008 Sep 11; 455(7210): 178-9. 5) McCarthy S et al. Nat Genet. 2009 Nov; 41(11): 1223-7. Epub 2009 Oct 25. 6) Helbig I et al. Nat Genet. 2009 Feb; 41(2): 160-2. Epub 2009 Jan 11. 7) Dibbens L et al. Hum Mol Genet. 2009 Oct 1; 18(19): 3626-31. Epub 2009 Jul 10. 8) Bochukova E et al. Nature. 2010 Feb 4; 463(7281): 666-70. Epub 2009 Dec 6. 9) Walters R et al. Nature. 2010 Feb 4; 463(7281): 671-5.

Thus, the statistical analysis and data modeled in Table 5, along with previous findings that rare CNVs cause disease (such as examples given in Tables 3, 4, and 6), demonstrate the capability of the NVE technology for systematic, genome-wide disease gene or locus discovery. Further, the findings in Table 6 using NVE principles were from data generated on a wide range of CNV detection platforms (BAC CGH, Oligo CGH, and SNP arrays from various vendors), thereby demonstrating the general applicability of the NVE technology in finding rare causative variants for common diseases. The NVE and CNV Beacon method can essentially be used for gene/causative biomarker discovery on any well-characterized, affected cohort. While finding causative mutations has immediate value in the development of diagnostic tests, such studies also lay the groundwork for realizing the promise of personalized medicine as targeted drugs cannot be developed without knowing the cause of an individual's particular subtype of a common disease. In this regard, the NVE and CNV Beacon method provide the means to rapidly expand the number and type of drug targets available to the pharmaceutical industry for drug development, which, in particular, can facilitate the development of novel RNAi therapeutics, expand the use of existing small molecule compound libraries, or repurpose existing FDA-approved therapies for off-label use. The NVE platform or the CNV Beacon method can be used in finding causative biomarkers of drug efficacy and adverse events, thereby enabling the development of companion tests that improve the dosing and safety of a drug.

One aspect of the invention is directed to accessing a set of data representing frequencies of one or more genetic variants in at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 subjects. In one embodiment, accessing involves computer executable logic, computer peripherals and computer hardware.

Another aspect of the invention provides a computer executable logic comprising a computer readable medium for enabling a processor to determine the relevance of one or more genetic variants in the genome of a subject. The computer executable logic comprises the processor receiving a set of data comprising frequency data for one or more genetic variants from the genome of at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 subjects. In another embodiment, the comparison is to one or more data sets comprising one or more cohorts wherein each cohort represents an ethnic group and wherein the frequencies of one or more genetic variants are comprised in data sets for each of one or more cohorts.

In one embodiment one or more data sets of the invention comprise frequency data for one or more cohorts, wherein each cohort represents an ethnic groups, and wherein each data set is a compilation of data obtained from at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 subjects. The computer executable logic further directs the processor to compare genetic variations from a subject, test subject or patient, to the preceding one or more data sets. In addition, the computer executable logic further directs the processor to provide output in an electronic or paper format which determines the significance of one or more genetic variants present in said subject, test subject, or patient, relative to a phenotype associated with a disease, condition or disorder. In another embodiment, the determination is whether a particular therapeutic should be eliminated, initiated or used in combination with another therapeutic, in designing a therapeutic regimen for said subject, test subject or patient.

In one embodiment, a computer-readable medium includes a medium suitable for transmission of a result of an analysis of an environmental or biological sample from a subject. The medium can comprise information on association of a genetic variant with a disease, condition or health of a subject, wherein such information is derived using the methods described herein.

In another embodiment, a computer executable logic provides instructions for executing a comparison between the information from a subject suspected of having a disease or condition with one or more genetic variants and a database of genetic variants in a normal population of subjects. In one embodiment the genetic variants were identified using the NVE platform or the CNV Beacon method. The computer executable logic uses data from the KMTs of the present invention, containing information about the frequencies of genetic variants in a normal population, a statistically significant population, a statistically relevant population, or a population of at least 50, 100, 200, 300, 400, 500, 600, 700, 800, 900, 1,000, 2,000, 3,000, 4,000, 5,000, 6,000, 7000, 8,000, 9,000, 10,000, 15,000, 20,000, 30,000, 40,000, 50,000, 60,000, 70,000, 100,000, 200,000, 500,000, 700,000, or 1,000,000 individuals. In a preferred embodiment, the computer executable logic uses data from the KMTs to determine if an observed genetic variant in a subject or cohort of subjects correlates to a phenotypic effect, e.g., disease or condition, or correlates to a normal variant, not correlated to a phenotypic effect, e.g., disease or condition. The computer executable logic can be utilized to identify in a subject or groups of subjects the efficacy a particular therapeutic agent, toxicity to a particular therapeutic drug (i.e., stratify patient profiles according to genomic structure variation).

The computer executable logic for determining such correlations is described as comprising an executable code, where the executable code is enabled to perform the method described above, comprising the acts of receiving data for one or more subjects or group of subjects, each providing a set of values or a data set of values; calculating a set of values for each of the data sets associated with each subject or group of subjects; selecting the data model that best fit the data, wherein the best model will be an indication that the frequencies of genetic variations observed in a subject or group of subjects as compared to the genetic variations of the KMTs so as to provide diagnostics. Such diagnostic determinations include correlations of such variants to phenotypic effects, including disease, disorders, efficacy or toxicity of candidate or actual therapeutic agents. Such determinations can be made by the computer executable logic or an end user, whereby results are displayed to an end user in either electronic or paper format.

Furthermore, any of the information or determinations described herein above (e.g., genetic variant frequencies for subjects, groups of subjects or KMTs providing variant frequency information for a statistically significant or any relevant population) can be stored on a medium capable of allowing computer executable logic. In some embodiments, a computer executable logic product is described comprising a computer usable medium having the computer executable logic (computer software program, including program code) stored therein. The computer executable logic, when executed by the processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

The KMTs can be provided as a computer program on a computer readable medium with computer executable logic for receiving information from the genome of one or more subjects, for comparing this information against the database of frequencies of one or more genetic variations and for providing an output on the assessment or result of the comparison. The databases of information on one or more genetic variations may be included in the computer program or accessible with the program. Being accessible rather than incorporated allows for easier updates and modifications of the databases.

A computer system which performs the comparisons is also provided and it includes the ability to input a subject's genomic information concerning one or more genetic variations. Ideally, this information may be supplied in a digital format from the screening assay, (e.g., sequencing. aCGH or PCR), directly to the computer system. The computer system also includes or has access to the databases (KMTs), performs the comparison and provides an output result of the comparison.

The business methods allow for the commercialization of the KMTs through licenses for access. Part of the commercial product may be the computer programs for inputting the data, running the most efficient comparisons and providing an output or just the computer program for accessing the KMTs. Frequently, the licenses may include provisions for back-licensing any additional genetic variations of significance identified with the computer program.

In one embodiment through collaborations with a pharmaceutical or biotech company, a R&D lab performs genome wide copy number scans of the company's clinical samples. The genome wide scans are then interpreted using the internal engine of normal variation in the population. The resulting information is copy number variations associated with efficacy and/or adverse reactions of drugs which may be finely targeted to that particular population of patients. These copy number variations are then used to identify one or more genetic variations also associated with the efficacy and/or adverse reactions of drugs using the methods disclosed herein. In one embodiment one or more assays designed to test for the presence or absence of the one or more genetic variations, which may be used by a pharmaceutical company to stratify human or non-human animal subjects in respective clinical trials.

A part of the personalized medicine aspect of the present invention includes therapeutic rescue. The pharmaceutical industry faces extremely high risks based on difficult realities. Some incredible facts about drug efficacy and toxicity emphasize the importance of a better tailored drug treatment regimen. The fifth leading cause of death is adverse drug reaction. Prescribed drugs do not work for patients 40-50% of the time they are prescribed. This translates to $60 billion annually in the U.S. and $20 billion in Japan, spent annually by consumers for ineffective treatments. The majority of potential drug candidates in a pharmaceutical company's clinical trial pipeline will never make it through the regulatory approval process because of lack of efficacy in enough patients or because of adverse effects in too many patients. This fact is a driver in the ever escalating costs for drug development and the consequent lost billions in development expenditures. A significant percentage of therapeutic responders or those that do not manifest adverse reactions are deprived of effective medicines when a drug does not gain regulatory approval based on traditional clinical trial design, where patients with genetic differences are lumped together with phenotype similarities. Therapeutics already on the market have a high risk of hurting patients because patient surveillance cannot easily be performed. The potential indirect medical costs, (i.e. hospitalization) for patients having relied on a medicine only to experience an adverse effect or lack of efficacy is a staggering financial figure.

All of these facts underscore the value of the KMTs which permit better evaluation of the genetic makeup of the patients and more focused treatment based on their genetic profile. It is broadly accepted that an individual's genetic makeup is responsible for differentiating a drug responder from a non-responder. It is also clear that an individual's genetic makeup is responsible for differentiating one's level of adverse effects to a particular drug therapy. Therefore, patient screening utilizing KMTs of the present invention provides for an effective evaluation distinguishing the important variations from those that do not have an effect on the phenotype and disease, or drug therapy. By utilizing all of this information, the cytogeneticist will generate a diagnostic recommendation from the KMTs. The advantage of the KMTs is their flexible and universal architecture allowing compatibility with other systems for data analysis and interpretation.

In one aspect of the invention, a database of genetic variants comprises a major feature of the KMTs of the present invention. In one embodiment, the database provides information on genetic variant frequencies from at least 50, 100, 200, 300, 400, 500, 600, 700, 800, 900, 1,000, 2,000, 3,000, 4,000, 5000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 individuals (e.g., normals, not displaying a targeted/identified phenotypic effect). In another embodiment, the database provides information on genetic variant frequencies from at least 10,000 individuals. In one embodiment the individuals are human subjects. In another embodiment, the database will provide such information for all subgroups of a population (e.g., ethnic groups in the human population), where designated subgroups can be based on age, gender, ethnicity, geography, race, or any other identifiable population group or subgroup.

In an alternative embodiment, the database provides information on genetic variant frequencies from at least 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 individuals, which are non-human animals (e.g., normal non-human animals, which do not display a targeted/identified phenotypic effect). Non-human animals include but are not limited to, mammals, birds, reptiles, amphibians, fish, insects and mollusks. More specifically it is envisioned that the database is derived from a species or breed of animal that is a disease model, is of commercial importance or is kept as a human companion. It is contemplated that a database will be created for a particular animal species or strain, wherein the animal is used as a model of disease or as a research tool. Such animals include but are not limited to: dogs, cats, rats, monkeys, chimpanzees, mice, rabbits, hamsters, gerbils, pigs and drosophila. It is also contemplated that a database will be created for an animal species or breed, wherein the animal has commercial importance, such as agricultural importance. Such animals include but are not limited to: cattle, bison, horses, donkeys, goats, sheep, pigs, alpacas, llamas, oxen, burros, deer, elk, moose, ostriches, emus, ducks, geese, chickens, partridges, quail, pheasant, mink, salmon, cod, catfish, herring, trout, bass, perch, flounder, sharks, tuna, blue crabs, Alaskan king crab, lobsters, crayfish, snails, clams, oysters, bees and alligators. It is further contemplated that a database will be created for an animal species, breed or strain that is a human companion. Such animals include but are not limited to: dogs, cats, horses, pot bellied pigs, ferrets, snakes, hamsters, gerbils, lizards, tropical fish, tarantulas, finches, parrots, parakeets, falcons, skunks, frogs and toads.

Non-Human Animal Genetic Variant Databases

The analytical methods disclosed herein can be also be used to survey the breeding populations of non-human animals. The production of databases of normal genetic variants for commercially important and companion animals, including cattle, sheep, pigs, horses, dogs or cats, will provide an important tool for screening breeding stock for causative mutations that are associated with decreased reproductive performance, particular decreases or other economically relevant or desired traits. In one embodiment a database of normal genetic variants for a particular non-human animal species or breed will be will be built and used to identify normally occurring polymorphisms which are not associated with quantitative trait loci. A non-human animal of interest, of the same species or breed as the database, which has a noteworthy phenotype (e.g. economically advantageous, disadvantageous or disease related) is then screened for one or more genetic variations using the methods disclosed herein. The results are then compared to the database. Genetic variations present principally in the genome of the non-human animal of interest allows for the identification of advantageous quantitative trait loci (QTL) or disease loci associated with a phenotype of the non-human animal of interest. Genetic variants associated with a specific QTL or disease loci can be used to screen other non-human animals of the same species or breed for said QTL or disease loci.

Information developed from databases of normal genetic variation in non-human animal species or breeds will allow further refinement of existing breeding practice by exclusion of undesirable individuals (e.g. individuals which are carriers for hereditary diseases or other undesirable phenotypes) from breeding programs. The linkage of specific genetic variations or chromosomal abnormalities to undesired phenotypes, which will improve the effectiveness of artificial insemination breeding programs.

Hereditary diseases are a growing concern within the animal breeding community Problems associated with inbreeding have been exacerbated since the introduction of modern breeding practices employing artificial insemination. This has resulted in an increase of recessive hereditary diseases carried by popular sires.

Hereditary diseases which can be linked to genetic variations are numerous and include, but are not limited to: epitheliogenesis imperfecta, epidermolysis bullosa, osteogenesis imperfecta, decreased fecundity, decreased milk production, elevated levels of bodyfat, autoimmune hemolytic anemia, basset hound thrombopathia, coagulation (bleeding) disorders, cyclic hematopoiesis, hemophilia, histiocytoma, histiocytosis, immune-mediated thrombocytopenia, lymphedema, phosphofructokinase (PFK) deficiency, pyruvate kinase (PK) deficiency, rare red blood cell abnormalities, thrombasthenic thrombopathia, Von Willebrand's disease, aortic stenosis, atrial septal defect, cardiomyopathy, mitral valve dysplasia, patent ductus arteriosus, vascular ring anomaly, portosystemic shunt, pulmonic stenosis, sick sinus syndrome, tetralogy of fallot, tricuspid dysplasia, ventricular septal defect, diabetes mellitus, growth-hormone responsive and adrenal sex-hormone dermatoses, hyperadrenocorticism (cushing's syndrome), hypoadrenocorticism (Addison's disease), hypothyroidism, j hyperparathyroidism, pituitary dwarfism (Hypopituitarism), cataracts, collie eye anomaly, corneal dystrophy, dermoids, ectropion, entropion, exposure keratopathy syndrome—exophthalmos, lagophthalmos, and/or macroblepharon, eyelash abnormalities—ectopic cilia, distichiasis, trichiasis, glaucoma, imperforate lacrimal punctum, keratoconjunctivitis sicca (KCS)—"dryeye", lens luxation, microphthalmia—ocular dysgenesis, optic nerve hypoplasia and micropapilla, pannus—chronic superficial keratitis, persistent pupillary membranes, progressive retinal atrophy, retinal dysplasia, third eyelid (nictitating membrane) abnormalities—"cherry eye", chronic hepatitis, cleft lip/palate, copper-associated hepatitis, copper toxicosis in Bedlington terriers, exocrine pancreatic insufficiency, gastric dilatation-volvulus (bloat), gluten (wheat)-sensitive enteropathy, histiocytic ulcerative colitis, hyperlipoproteinemia, immunoproliferative (Basenji) enteropathy/lymphocytic-plasmacytic enteritis, intestinal lymphangiectasia, megaesophagus, pancreatitis, perianal fistula, portosystemic shunt, protein-losing enteropathy, protein-losing enteropathy and nephropathy (soft-coated Wheaten terrier), pyloric stenosis, small intestinal bacterial overgrowth (SIBO), atopy, autoimmune hemolytic anemia, bullous pemphigoid, complement deficiency, cyclic hematopoiesis, german shepherd pyoderma, immune-mediated thrombocytopenia, lupus erythematosus, pemphigus, selective IgA deficiency, severe combined immunodeficiency, weimaraner immunodeficiency, cerebellar abiotrophy (ataxia), cerebellar hypoplasia, cervical vertebral instability (Wobbler syndrome), congenital deafness and vestibular disease, deafness, degenerative myelopathy, globoid cell leukodystrophy, hypo-/dysmyelinogenesis ("shaking pup"), hydrocephalus, idiopathic epilepsy, intervertebral disk disease, laryngeal paralysis, leukodystrophies (Such as: demyelinating myelopathy, hereditary ataxia central axonopathy, myelomalacia, spongiform leukodystrophy, fibrinoid leukodystrophy), lissencephaly, lysosomal storage diseases (such as: ceroid lipofuscinosis, fucosidosis, glucocerebrosidosis, glycogen storage disease type III, GM1 gangliosidosis, GM2 gangliosidosis, mucopolysaccharidosis I, sphingomyelinosis), meningitis, meningoencephalitis, myasthenia gravis, myelodysplasia (spinal dysraphism), neuroaxonal dystrophy, peripheral neuropathies (such as: distal polyneuropathy, giant axonal neuropathy, idiopathic polyneuropathy, hypertrophic neuropathy, progressive axonopathy, sensory neuropathy, laryngeal paralysis-polyneuropathy complex, megaesophagus), shaker dog syndrome, scotty cramp, spina bifida, spinal muscular atrophy/motor neuron diseases (such as: spinal muscular atrophy, focal spinal muscular atrophy, hereditary progressive spinal muscular atrophy, motor neuron disease, multisystemic chromatolytic neuronal degeneration), vertebral stenosis, brachycephalic syndrome, hypoplastic trachea, laryngeal paralysis, tracheal collapse, acanthosis nigricans, acral lick dermatitis/granuloma, acral mutilation syndrome, atopy/allergic inhalant dermatitis, bullous pemphigoid, canine acne, colour dilution alopecia, congenital hypotrichosis, cutaneous asthenia (Ehlers-Danlos syndrome), cutaneous mucinosis, dalmatian bronzing syndrome, demodicosis/demodectic mange, dermatomyositis and ulcerative dermatosis, dermoid sinus, ectodermal defect, epidermal dysplasia, epidermolysis bullosa, follicular dysplasias (also black hair follicular dysplasia), fold dermatitis/pyoderma, footpad disorder in the German shepherd, German shepherd pyoderma, growth hormone responsive dermatosis, ichthyosis, lethal acrodermatitis, lupus erythematosus, lymphedema, lupoid dermatosis, malassezia dermatitis/otitis, nodular dermatofibrosis (nevi) and renal cystadenocarcinoma, pattern baldness, pemphigus, perianal fistula, psoriasiform-lichenoid dermatosis, Schnauzer comedo syndrome, sebaceous adenitis, seborrhea, vitamin A-responsive dermatosis, vitiligo, Zinc-responsive dermatosis, cryptorchidism, disorders of sexual development—sexual reversal, familial kidney disease (such as: hereditary nephritis/nephropathy, renal dysplasia, renal amyloidosis), fanconi syndrome, nodular dermatofibrosis and renal cystadenocarcinoma, urolithiasis (stones), exertional rhabdomyolysis, polysaccharide storage myopathy, leukocyte adhesion deficiency, hereditary zinc deficiency, protoporphyria, dilated cardiomyopathy, regional dermal asthenia, elliptocytosis, equine motor neuron disease (Shivers), and Wobbler disease.

In an alternative embodiment, the database provides information on genetic variant frequencies from at least 50, 100, 200, 300, 400, 500, 600, 700, 800, 900, 1,000, 2,000, 3,000, 4,000, 5000, 6,000, 7,000, 8,000, 9,000, 10,000, 15,000, 20,000, 30,000, 40,000, 50,000, 60,000, 70,000, 100,000, 200,000, 500,000, 700,000, or 1,000,000 individuals, which are plants. Plants include vascular and non-vascular plants, including Arabidopsis, corn, wheat, rice, sugar cane, barley, cotton, algae, seaweed and others.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

EXAMPLES

Example 1

Samples will be taken from at least one hundred patients with Parkinson's disease. Nucleic acid will be isolated from the samples. Array Comparative Genomic Hybridization will be used to detect copy number variants from the samples. The information on copy number variants from the samples will be inputted into a computer. The computer will compare the information on copy number variants from the sample to information in a database. The information in the database is information on the frequency of copy number variants from at least 1,000 subjects that have not been diagnosed with Parkinson's disease. The statistical significance of the correlation of Parkinson's disease with one or more copy number variants in the samples from the Parkinson's disease patients will be determined. A copy number variation will be identified in a sub-population of Parkinson's disease patients that is not in the database of information on subjects that do not have Parkinson's disease.

Next, nucleic acid sequence upstream and downstream of the copy number variation, as well as within the copy number variation itself, will be sequenced using a next generation sequencing platform in the samples from Parkinson's disease patients that may or may not have the copy number variation. The corresponding genome region will also be sequenced in larger numbers of subjects that do not have Parkinson's disease (either clinical signs or diagnosis). At least one genetic variant will be identified in a non-coding or coding region of a gene near the copy number variation in one or more subjects that have Parkinson's disease that may or may not have the copy number variation. Then at least one genetic variant will not be found in the subjects that do not have Parkinson's disease or will not be present in at statistically significant levels. It can be appreciated by those skilled in the art that one subject diagnosed with a disease, such as Parkinson's disease, may have more than one genetic variants causing or impacting their disease.

Example 2

Several assays are performed to determine if the mutation identified in Example 1 affects the function of the gene in which the mutation resides. First, a computer will be used to determine if there is a change in the amino acid sequence of the predicted protein product of the gene. Second, the mRNA expression levels of the gene will be compared in samples from patients with the mutation and in samples from subjects without the mutation. Third, an activity assay will be performed using a protein with sequence derived from a subject without the single base mutation and a protein with sequence containing the single base mutation. The assay will be used to determine if the mutation affects the activity of the protein. Fourth, X-ray crystallography can be performed on a protein with sequence derived from a subject without the mutation and on a protein with amino acid sequence derived from a patient with the mutation. This structural study will be used to determine if the mutation affects the three dimensional structure of the protein or if the mutation affects the properties of a binding site on the surface of the protein.

Example 3

Next, a drug screen will be performed to identify compounds that can treat Parkinson's disease with the genetic variant identified in Example 1 and validated in Example 2. Multiple compounds (e.g. up to 50,000 compounds) will be screened of which one or more candidates will be identified to treat Parkinsons disease with the genetic variant identified in Example 1 and validated in Example 2. Clinical trials will be performed and one compound will be found to be safe and effective. The one compound will be found to be efficacious in Parkinson's disease patients that have the genetic variant identified in Example 1 and not in Parkinson's disease patients that do not have the genetic variant identified in Example 1.

New Parkinson's disease patients will be screened for the mutation. A Parkinson's disease patient that has the genetic variant identified in Example 1 will be prescribed the compound.

REFERENCES

Berkel S. et al. Nat Genet. 2010 June; 42(6):489-91
Bochukova E. et al. Nature. 2010 Feb. 4; 463:666-70
Dibbens L. et al. Hum Mol Genet. 2009 Oct. 1; 18:3626-31
Helbig I. et al. Nat Genet. 2009 February; 41:160-2
International Schizophrenia Consortium Nature. 2008 Sep. 11; 455:237-41
Kumar R. et al. Hum Mol Genet. 2008 Feb. 15; 17:628-38
McCarthy S. et al. Nat Genet. 2009 November; 41:1223-7),
Roohi J. et al. J Med Genet. 2009 March; 46:176-82
Stefansson H. et al. Nature. 2008 Sep. 11; 455:178-9
Walsh T. et al. JAMA. 2006 Mar. 22; 295(12):1379-88;
Walsh T. et al. Proc Natl Acad Sci USA. 2010 Jul. 13; 107 (28):12629-33.
Walters R. et al. Nature. 2010 Feb. 4; 463:671-5
Weiss L. et al. N Engl J. Med. 2008 Feb. 14; 358:667-75

What is claimed is:

1. A method of determining a pathogenic genetic variant of a disease or condition in one or more subjects affected by the disease or condition comprising:
   (a) screening DNA from a subject with PCR, array Comparative Genomic Hybridization, sequencing, SNP genotyping, an Invader assay, or Fluorescence in Situ Hybridization, to provide information on one or more copy number variants; wherein the subject is affected by the disease or condition;
   (b) comparing via a computer, the information on the one or more copy number variants from the subject's genome to a compilation of data comprising frequencies of copy number variants in at least 100 subjects unaffected by the disease or condition, wherein the computer comprises computer executable logic that provides instructions for executing the comparison;
   (c) determining a statistical significance of the one or more copy number variants to a disease or condition associated with a genotype from the comparison of step (b), or determining whether the one or more copy number variants is present in the subject's genome but absent or present at lower frequency in the compilation of data from the comparison of step (b);
   (d) sequencing the one or more copy number variants or genome regions encompassing the one or more copy number variants determined according to step (c), from the DNA of one or more subjects affected by the disease or condition, to identify a first set of one or more genetic variants;
   (e) sequencing the one or more copy number variants or one or more genome regions encompassing the one or more copy number variants determined according to step (c), from the DNA of one or more subjects unaffected by the disease or condition, to identify a second set of one or more genetic variants;
   (f) determining whether a genetic variant of the first set of one or more genetic variants is a pathogenic genetic variant or a benign genetic variant by comparing the first set of one or more genetic variants to the second set of one or more genetic variants.

2. The method of claim 1, wherein the information on the one or more copy number variants is genome-wide.

3. The method of claim 1, wherein the compilation of data comprising frequencies of copy number variants comprises data from at least 1,000, 3,000, 5,000, or 10,000 subjects unaffected by the disease or condition.

4. The method of claim 1, further comprising screening the second set of one or more genetic variants of step (d) from the DNA of at least 100, 200, 500, 1,000, 2,000, 3,000, 4,000, or 5,000 subjects affected by the disease or condition by PCR, junction fragment PCR, multiplex ligation-dependent probe amplification (MLPA), Invader assay, or genotyping microarrays.

5. The method of claim 1, further comprising screening the first set of one or more genetic variants of step (e) from the DNA of at least 100, 200, 500, 1,000, 2,000, 3,000, 5,000, 10,000, or 20,000 subjects unaffected by the disease or condition by PCR, junction fragment PCR, multiplex ligation-dependent probe amplification (MLPA), Invader assay, or genotyping microarrays.

6. The method of claim 1, further comprising assessing the functional impact of the one or more copy number variants, the first set of one or more genetic variants, or the second set of one or more genetic variants of steps (a), (d), or (e) on an RNA or protein product resulting from a gene or functional region of the genome that is near or contains the one or more copy number variants, the first set of one or more genetic variants, or the second set of one or more genetic variants using an in silico method to identify the pathogenic genetic variant or the benign genetic variant in the one or more subjects affected or the one or more subjects unaffected by the disease or condition.

7. The method of claim 1, further comprising assessing the functional impact of the one or more copy number variants, the first set of one or more genetic variants, or the second set of one or more genetic variants of steps (a), (d), or (e) on a gene or functional region of the genome that is near or contains the one or more copy number variants, the first set of one or more genetic variants, or the second set of one or more genetic variants using an in vitro method or assays to identify the pathogenic genetic variant or the benign genetic variant in the one or more subjects affected or the one or more subjects unaffected by the disease or condition.

8. The method of claim 1, further comprising assessing the functional impact of the one or more copy number variants, the first set of one or more genetic variants, or the second set of one or more genetic variants of steps (a), (d), or (e) on a gene or functional region of the genome that is near or contains the one or more copy number variants, the first set of one or more genetic elements, or the second set of one or more genetic elements, using an RNAi screening method or assay to identify the pathogenic genetic variant or the benign genetic variant in the one or more subjects affected or the one or more subjects unaffected by the disease or condition.

9. The method of claim 1, further comprising:
   (g) transcriptome sequencing one or more tissues derived from the one or more subjects affected by the disease or condition to provide information on one or more RNA variants resulting from the one or more copy number variants or genome regions encompassing the one or more copy number variants;
   (h) transcriptome sequencing one or more tissues derived from 20 or more subjects unaffected by the disease or condition to provide information on one or more RNA variants resulting from the one or more copy number variants or genome region(s) encompassing the one or more copy number variants;
   (i) assessing the functional impact of the one or more RNA variants of steps (g) and (h) on one or more protein products or regulatory RNA products resulting from the one or more RNA variants using an in silico or an in vitro method to identify the pathogenic genetic variant or the benign genetic variant in the one or more subjects affected or the one or more subjects unaffected by the disease or condition.

10. The method of claim 1, further comprising:
    (g) performing epigenetic analysis of one or more tissues derived from the one or more subjects affected by the disease or condition to provide information on the epigenetic state of the region within the one or more copy number variants or genome regions encompassing the one or more copy number variants;
    (h) performing epigenetic analysis one or more tissues derived from 20 or more subjects unaffected by the disease or condition to provide information on the epigenetic state of the region within the one or more copy number variants or genome regions encompassing the one or more copy number variants;
    (i) assessing the functional impact of the epigenetic states of steps (g) and (h) on one or more RNA or protein products resulting from the epigenetic states contained within or near a gene or functional region of the genome using an in silico or an in vitro method to identify the pathogenic genetic variant or the benign genetic variant in the one or more subjects affected or the one or more subjects unaffected by the disease or condition.

11. The method of any one of claim 6, 7, 8, 9, or 10, further comprising determining a statistical significance of the pathogenic genetic variant.

12. The method of claim 1, further comprising assessing the functional impact of the one or more copy number variants, the first set of one or more genetic variants, or the second set of one or more genetic variants of steps (a), (d), or (e) on an RNA or protein product resulting from a gene or functional region of the genome that is near or contains the one or more copy number variants, the first set of one or more genetic variants, or the second set of one or more genetic variants using two or more of an in silico method, an in vitro method, an RNAi screening method, transcriptome sequencing, and an epigenetic analysis to identify the pathogenic genetic variant or the benign genetic variant in the one or more subjects affected or the one or more subjects unaffected by the disease or condition.

13. The method of claim 1, further comprising:
   screening DNA from a test subject with the disease or condition with an assay,
   producing an electronic or hard copy report indicating whether the pathogenic genetic variant is present or absent in the DNA from the test subject.

14. The method of claim 13, wherein the pathogenic genetic variant comprises a plurality of pathogenic genetic variants, wherein only a subset of the plurality of pathogenic genetic variants is tested to diagnose the disease or condition in a test subject, wherein the subset of pathogenic genetic variants has been previously determined based on:
   ascertainment of the frequency of occurrence of the pathogenic genetic variants of the subset of pathogenic genetic variants in subjects affected and unaffected with the disease or condition.

15. The method of claim 13, wherein the DNA from the test subject is screened only if the test subject does not have a subset of pathogenic genetic variants previously determined based on
   ascertainment of the frequency of occurrence of the pathogenic genetic variants of the subset of pathogenic genetic variants in subjects affected and unaffected with the disease or condition.

16. The method of claim 13, wherein the test subject is a newborn.

17. The method of claim 14, wherein the test subject is a newborn.

18. The method of claim 1, further comprising:
   (g) sequencing a region upstream and/or downstream of the one or more copy number variants determined according to step (c), in the one or more subjects affected by the disease or condition, to identify a first set of one or more upstream/downstream genetic variants;
   (h) sequencing a region upstream and/or downstream of the one or more copy number variants determined according to step (c), in the one or more subjects unaffected by the disease or condition, to identify a second set of one or more upstream/downstream genetic variants; and
   (i) determining whether a genetic variant of the first set of one or more upstream and/or downstream genetic variants is a pathogenic genetic variant or a benign genetic variant by comparing the first set of one or more upstream and/or downstream genetic variants to the second set of one or more upstream/downstream genetic variants.

19. The method of claim 1, further comprising assessing the functional impact of the one or more copy number variants, the first set of one or more genetic variants, or the second set of one or more genetic variants of steps (a), (d), or (e) on a DNA sequence corresponding to a functional region of the DNA from the subject using an in silico method to identify the pathogenic genetic variant or benign genetic variants in the one or more subjects affected or the one or more subjects unaffected by the disease or condition.

20. The method of claim 1, further comprising assessing the functional impact of the one or more copy number variants, the first set of one or more genetic variants, or the second set of one or more genetic variants of steps (a), (d), or (e) on a DNA sequence corresponding to a functional region of the DNA from the subject using an in vitro method to identify the pathogenic genetic variant or benign genetic variant in the one or more subjects affected or the one or more subjects unaffected by the disease or condition.

21. The method of claim 1, further comprising assessing the functional impact of the one or more copy number variants, the first set of one or more genetic variants, or the second set of one or more genetic variants of steps (a), (d), or (e) on an RNA or protein product resulting from a gene or functional region of the DNA from the subject near or containing the one or more copy number variants, the first set of one or more genetic variants, or the second set of one or more genetic variants using structural biology methods to identify the pathogenic genetic variant or benign genetic variant in the one or more subjects affected or the one or more subjects unaffected by the disease or condition.

22. The method of claim 1, further comprising assessing in silico if an RNA or protein product resulting from a gene near or containing the one or more copy number variants, the first set of one or more genetic variants, or the second set of genetic variants of steps (a), (d), or (e) is a known drug target, impacts a known drug target's mechanism of action, is a binding partner of a known drug target, or is linked to a known drug target via pathway analysis.

23. The method of claim 1, wherein the one or more copy number variants or the first set of one or more genetic variants of steps (a) or (d) occur within a gene or impact the expression of a gene, wherein the gene is qualified as a drug target via an in silico or an in vitro method for potentially treating a subject affected by the disease or condition.

24. The method of claim 1, wherein the one or more copy number variants or the first set of one or more genetic variants of steps (a) or (d) occur within a gene or impact the expression of a gene, wherein a binding partner of the gene is qualified as a drug target via an in silico or an in vitro method for potentially treating a subject affected by the disease or condition.

25. The method of claim 1, wherein the one or more copy number variants or the first set of one or more genetic variants of steps (a) or (d) occur within a gene or impact the expression of a gene, wherein the gene's pathway interaction is identified to another gene that is qualified as a drug target via an in silico or an in vitro method for potentially treating a subject affected by the disease or condition.

26. The method of any of claims 23-25, further comprising screening a library of small molecule compounds libraries to identify one or more small molecule compounds that impact the activity or expression of the drug target.

27. The method of claim 1, further comprising using tissue from the one or more subjects with the disease or condition containing the one or more copy number variants or first set of one or more genetic variants of steps (a) or (d) to generate an induced pluripotent stem cell for functional validation of the one or more copy number variants or the first set of one or more genetic variants of steps (a) or (d) using an in vitro method.

28. The method of claim 1, further comprising:
(g) transcriptome sequencing one or more tissues derived from the one or more subjects affected by the disease or condition to provide information on one or more RNA variants resulting from the one or more copy number variants or genome regions encompassing the one or more copy number variants;
(h) transcriptome sequencing one or more tissues derived from 20 or more subjects unaffected by the disease or condition to provide information on one or more RNA variants resulting from the one or more copy number variants or genome regions encompassing the one or more copy number variants; and
(i) assessing the relative expression level or number of the one or more RNA variants of steps (g) and (h) to identify the pathogenic genetic variant or benign genetic variant in the one or more subjects affected or the one or more subjects unaffected by the disease or condition.

29. The method of claim 1, further comprising:
(g) performing a microarray analysis on one or more tissues derived from the one or more subjects affected by the disease or condition to provide information on one or more RNA variants resulting from the one or more copy number variants or genome regions encompassing the one or more copy number variants;
(h) performing a microarray analysis on one or more tissues derived from 20 or more subjects unaffected by the disease or condition to provide information on one or more RNA variants resulting from the one or more copy number variants or genome regions encompassing the one or more copy number variants; and
(i) assessing the relative expression level or number of the one or more RNA variants of steps (g) and (h) to identify the pathogenic genetic variant or benign genetic variant in the one or more subjects affected or the one or more subjects unaffected by the disease or condition.

30. The method of claim 1, further comprising:
(g) performing a reverse transcriptase PCR analysis on one or more tissues derived from the one or more subjects affected by the disease or condition to provide information on one or more RNA variants resulting from the one or more copy number variants or genome regions encompassing the one or more copy number variants;
(h) performing a reverse transcriptase PCR analysis on one or more tissues derived from 20 or more subjects unaffected by the disease or condition to provide information on one or more RNA variants resulting from the one or more copy number variants or genome regions encompassing the one or more copy number variants; and
(i) assessing the relative expression level or number of the one or more RNA variants of steps (g) and (h) to identify the pathogenic genetic variant or benign genetic variant in the one or more subjects affected or the one or more subjects unaffected by the disease or condition.

31. The method of claim 1, further comprising:
(g) performing an Invader assay analysis on one or more tissues derived from the one or more subjects affected by the disease or condition to provide information on one or more RNA variants resulting from the one or more copy number variants or genome regions encompassing the one or more copy number variants;
(h) performing an Invader analysis on one or more tissues derived from 20 or more subjects unaffected by the disease or condition to provide information on one or more RNA variants resulting from the one or more copy number variants or genome regions encompassing the one or more copy number variants;
(i) assessing the relative expression level or number of the one or more RNA variants of steps (g) and (h) to identify the pathogenic genetic variant or benign genetic variant in the one or more subjects affected or the one or more subjects unaffected by the disease or condition.

32. The method of claim 1, wherein the information from step (c) or the determination from (f) is used to enroll a subject with the disease or condition in a therapeutic clinical trial or exclude a subject with the disease or condition from a therapeutic clinical trial.

33. The method of claim 1, wherein the information from step (c) or the determination from (f) is used to enroll a subject with the disease or condition in a diagnostic clinical trial or exclude a subject with the disease or condition from a diagnostic clinical trial.

34. The method of claim 1, wherein the information from step (a) or information about the first set of genetic variants from step (d) is stored on a computer comprising computer executable logic that provides instructions for executing the comparisons in steps (c) and (f).

35. The method of claim 34, wherein the stored information from step (a) or (d) is stored as part of, or linked to, the one or more subjects affected by the disease or conditions' electronic medical record or electronic health record.

36. The method of claim 1, wherein the screening is with array Comparative Genomic Hybridization.

37. A nontransitory computer readable medium comprising instructions for determining a pathogenic genetic variant of a disease or condition in one or more subjects affected by the disease or condition, the instructions comprising the steps of:
(a) screening DNA from a subject with PCR, array Comparative Genomic Hybridization, sequencing, SNP genotyping, an Invader assay, or Fluorescence in Situ Hybridization to provide information on one or more copy number variants; wherein the subject is affected by the disease or condition;
(b) comparing via a computer comprising the nontransitory computer readable medium, the information on the one or more copy number variants from the subject's genome to a compilation of data comprising frequencies of copy number variants in at least 100 subjects unaffected by the disease or condition, wherein the computer comprises computer executable logic that provides instructions for executing the comparison;
(c) determining a statistical significance of the one or more copy number variants to a disease or condition associated with a genotype from the comparison of step (b), or determining whether the one or more copy number variants is present in the subject's genome but absent or present at lower frequency in the compilation of data from the comparison of step (b);
(d) sequencing the one or more copy number variants or genome regions encompassing the one or more copy number variants determined according to step (c), from the DNA of one or more subjects affected by the disease or condition, to identify a first set of one or more genetic variants;
(e) sequencing the one or more copy number variants or one or more genome regions encompassing the one or more copy number variants determined according to step (c), from the DNA of one or more subjects unaffected by the disease or condition, to identify a second set of one or more genetic variants;

(f) determining whether a genetic variant of the first set of one or more genetic variants is a pathogenic genetic variant or a benign genetic variant by comparing the first set of one or more genetic variants to the second set of one or more genetic variants.

38. A computer system comprising instructions for determining a pathogenic genetic variant of a disease or condition in one or more subjects affected by the disease or condition, the system comprising instructions for executing the steps of:
   (a) screening DNA from a subject with PCR, array Comparative Genomic Hybridization, sequencing, SNP genotyping, an Invader assay, or Fluorescence in Situ Hybridization to provide information on one or more copy number variants; wherein the subject is affected by the disease or condition;
   (b) comparing via the computer system, the information on the one or more copy number variants from the subject's genome to a compilation of data comprising frequencies of copy number variants in at least 100 subjects unaffected by the disease or condition, wherein the computer comprises computer executable logic that provides instructions for executing the comparison;
   (c) determining a statistical significance of the one or more copy number variants to a disease or condition associated with a genotype from the comparison of step (b), or determining whether the one or more copy number variants is present in the subject's genome but absent or present at lower frequency in the compilation of data from the comparison of step (b);
   (d) sequencing the one or more copy number variants or genome regions encompassing the one or more copy number variants determined according to step (c), from the DNA of one or more subjects affected by the disease or condition, to identify a first set of one or more genetic variants;
   (e) sequencing the one or more copy number variants or one or more genome regions encompassing the one or more copy number variants determined according to step (c), from the DNA of one or more subjects unaffected by the disease or condition, to identify a second set of one or more genetic variants;
   (f) determining whether a genetic variant of the first set of one or more genetic variants is a pathogenic genetic variant or a benign genetic variant by comparing the) first set of one or more genetic variants to the second set of one or more genetic variants.

39. The method of claim 1, wherein the one or more subjects unaffected by the disease or condition comprise at least 1,000 subjects unaffected by the disease or condition.

40. The method of claim 1, wherein the one or more subjects unaffected by the disease or condition comprise at least 2,000 subjects unaffected by the disease or condition.

41. The method of claim 1, wherein the one or more subjects unaffected by the disease or condition comprise at least 3,000 subjects unaffected by the disease or condition.

42. The method of claim 1, wherein the one or more subjects unaffected by the disease or condition comprise at least 5,000 subjects unaffected by the disease or condition.

\* \* \* \* \*